(12) United States Patent
Longo et al.

(10) Patent No.: US 11,376,140 B1
(45) Date of Patent: *Jul. 5, 2022

(54) MEDICAL IMPLANTS WITH STRUCTURAL MEMBERS HAVING BARBS FOR RETAINING RADIOPAQUE MARKERS

(71) Applicant: Vesper Medical, Inc., Wayne, PA (US)

(72) Inventors: Michael Longo, Glenmoore, PA (US); Christopher Turek, West Chester, PA (US); Timothy O'Neil, King of Prussia, PA (US); Daniel Alexander, Huntingdon Valley, PA (US)

(73) Assignee: Vesper Medical, Inc., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/475,527

(22) Filed: Sep. 15, 2021

Related U.S. Application Data

(63) Continuation of application No. 17/214,232, filed on Mar. 26, 2021, now Pat. No. 11,147,694.

(51) Int. Cl.
*A61F 2/82* (2013.01)
*A61F 2/848* (2013.01)

(52) U.S. Cl.
CPC ............ *A61F 2/82* (2013.01); *A61F 2/848* (2013.01); *A61F 2002/8483* (2013.01); *A61F 2220/0016* (2013.01); *A61F 2220/0033* (2013.01); *A61F 2230/0006* (2013.01); *A61F 2230/0008* (2013.01); *A61F 2230/0067* (2013.01); *A61F 2230/0069* (2013.01); *A61F 2250/0098* (2013.01)

(58) Field of Classification Search
CPC ...... A61F 2250/0096–0098; A61F 2220/0033; A61F 2250/0068
See application file for complete search history.

(56) References Cited

U.S. PATENT DOCUMENTS

| | | | |
|---|---|---|---|
| 5,632,771 A | 5/1997 | Boatman et al. | |
| 5,725,572 A | 3/1998 | Lam et al. | |
| 5,824,042 A | 10/1998 | Lombardi et al. | |

(Continued)

FOREIGN PATENT DOCUMENTS

| | | |
|---|---|---|
| DE | 102005019612 A1 | 11/2006 |
| EP | 1356789 A1 | 10/2003 |

(Continued)

OTHER PUBLICATIONS

International Search Report and the Written Opinion issued for Application No. PCT/US2021/051231, dated Jan. 4, 2022.

(Continued)

*Primary Examiner* — Rebecca S Preston
(74) *Attorney, Agent, or Firm* — Meunier Carlin & Curfman LLC

(57) ABSTRACT

A medical implant may include a structural member and a radiopaque marker. The structural member may include a first surface, a second surface disposed opposite the first surface, an opening extending from the first surface to the second surface and defining a central axis, and a plurality of barbs extending into the opening toward the central axis. The barbs may be spaced apart from one another and spaced apart from each of the first surface and the second surface. The radiopaque marker may be disposed within the opening.

20 Claims, 6 Drawing Sheets

(56) References Cited

U.S. PATENT DOCUMENTS

| | | | |
|---|---|---|---|
| 6,022,374 A * | 2/2000 | Imran | A61F 2/91 623/1.34 |
| 6,334,871 B1 | 1/2002 | Dor et al. | |
| 6,402,777 B1 | 6/2002 | Globerman et al. | |
| 6,464,720 B2 | 10/2002 | Boatman et al. | |
| 6,899,914 B2 | 5/2005 | Schaldach et al. | |
| 8,211,163 B2 | 7/2012 | Dakin et al. | |
| 8,425,589 B2 | 4/2013 | Hegel | |
| 8,475,519 B2 | 7/2013 | Hegel et al. | |
| 8,475,520 B2 | 7/2013 | Wack et al. | |
| 8,752,268 B2 | 6/2014 | Wu | |
| 9,532,888 B2 | 1/2017 | Dugan et al. | |
| 9,700,443 B2 | 7/2017 | Lumauig et al. | |
| 9,737,368 B2 | 8/2017 | Lumauig | |
| 9,999,527 B2 | 6/2018 | Pacetti et al. | |
| 10,610,387 B2 | 4/2020 | Lumauig et al. | |
| 11,147,694 B1 * | 10/2021 | Longo | A61F 2/82 |
| 2002/0143386 A1 | 10/2002 | Davila et al. | |
| 2002/0193867 A1 | 12/2002 | Gladdish, Jr. et al. | |
| 2003/0060872 A1 | 3/2003 | Gomringer et al. | |
| 2004/0088039 A1 | 5/2004 | Lee et al. | |
| 2005/0060025 A1 | 3/2005 | Mackiewicz et al. | |
| 2005/0172471 A1 | 8/2005 | Vietmeier | |
| 2006/0259129 A1 | 11/2006 | Hegel | |
| 2007/0043429 A1 * | 2/2007 | Hegel | A61F 2/82 623/1.15 |
| 2007/0266542 A1 | 11/2007 | Melsheimer | |
| 2008/0288046 A1 | 11/2008 | Hemerick et al. | |
| 2012/0089219 A1 | 4/2012 | Fircho et al. | |
| 2014/0013574 A1 | 1/2014 | Giasolli | |
| 2017/0172768 A1 * | 6/2017 | Ta | A61F 2/958 |
| 2017/0231646 A1 | 8/2017 | Epstein et al. | |

FOREIGN PATENT DOCUMENTS

| | | |
|---|---|---|
| EP | 1656905 B1 | 12/2006 |
| WO | 99/30643 A1 | 6/1999 |

OTHER PUBLICATIONS

International Search Report and Written Opinion issued for Application No. PCT/US2021/049198, dated Jan. 12, 2022.

* cited by examiner

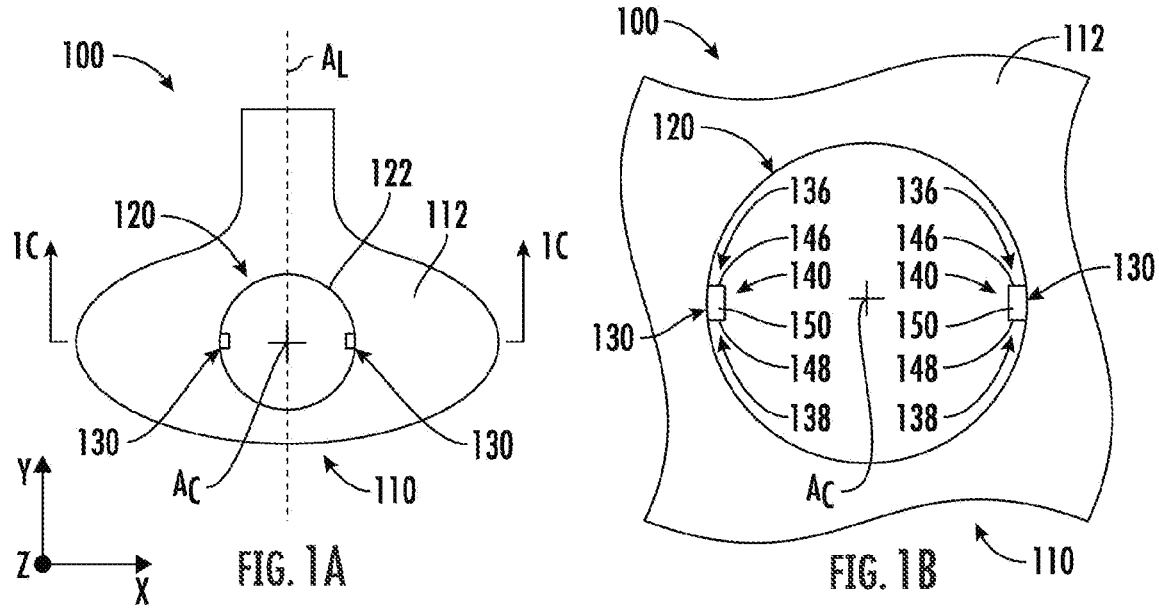
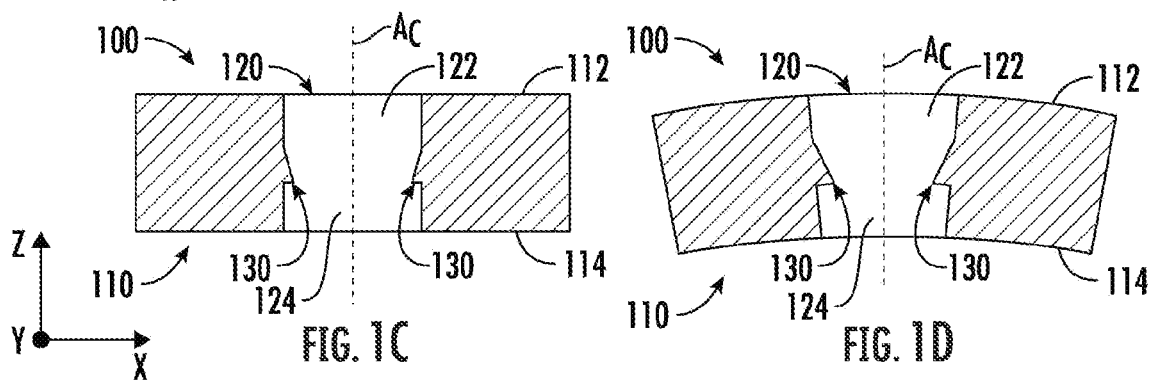
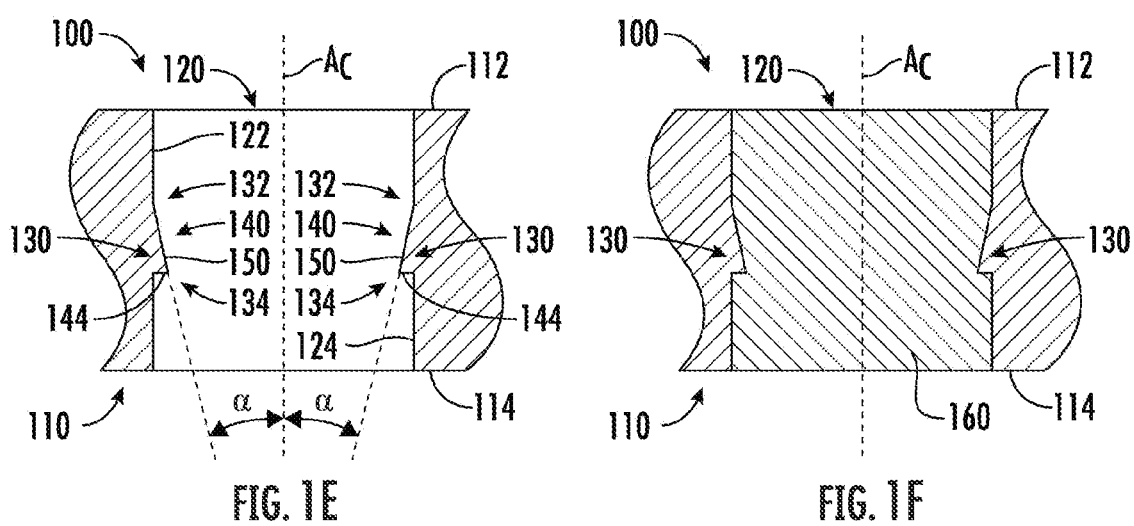
FIG. 1A  FIG. 1B  FIG. 1C  FIG. 1D  FIG. 1E  FIG. 1F

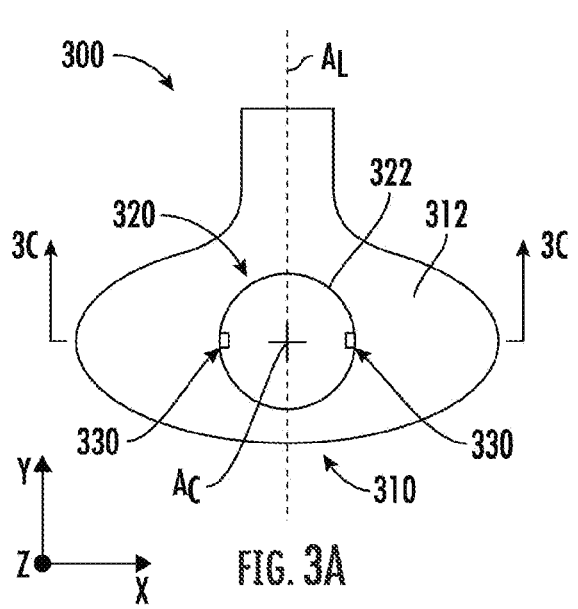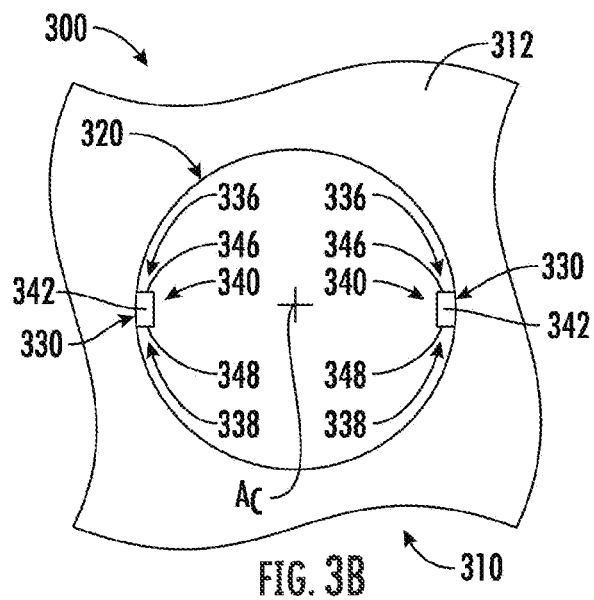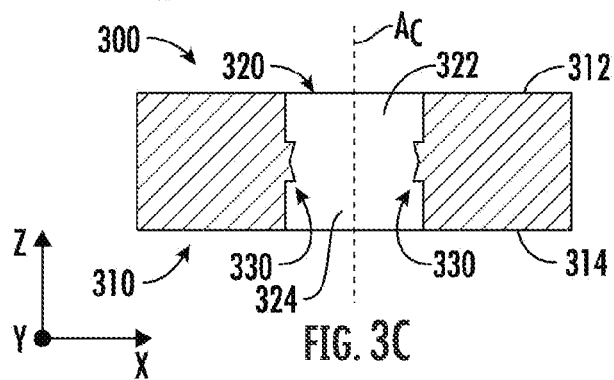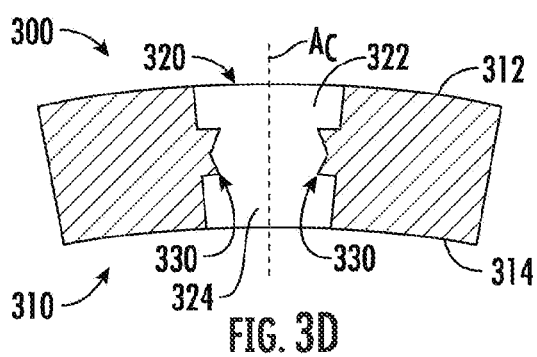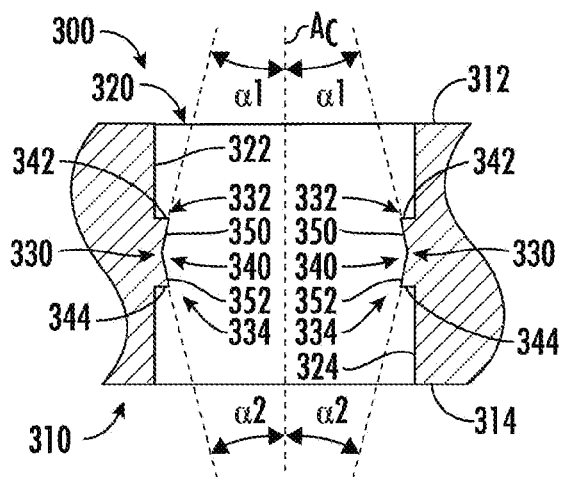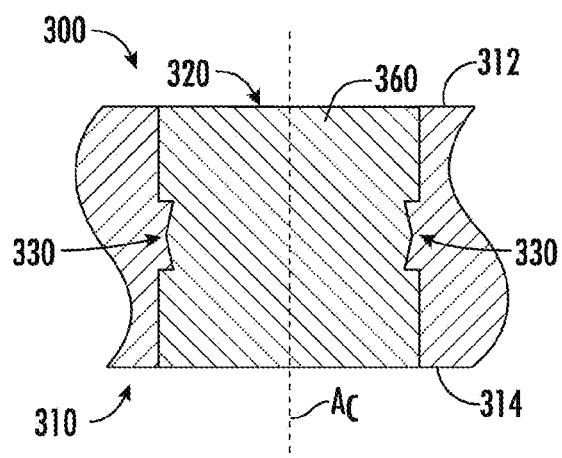

MEDICAL IMPLANTS WITH STRUCTURAL MEMBERS HAVING BARBS FOR RETAINING RADIOPAQUE MARKERS

CROSS-REFERENCE TO RELATED APPLICATIONS

This application is a continuation of U.S. patent application Ser. No. 17/214,232, filed Mar. 26, 2021, which is hereby incorporated by reference in its entirety for all purposes as if fully set forth herein.

FIELD OF THE DISCLOSURE

The present disclosure relates generally to medical implants and more particularly to medical implants with structural members having barbs for retaining radiopaque markers.

BACKGROUND OF THE DISCLOSURE

Various types of medical implants may include one or more radiopaque markers to facilitate visualization of the implant relative to the anatomy of a subject during and/or after implantation. For example, stents, such as intravascular stents, often may include one or more radiopaque markers connected to one or more structural members of the stent. A radiopaque marker generally may be positioned and secured within an opening or recess of a structural member of a medical implant. The radiopaque marker often may be formed of a precious or other rare earth metal, while the structural member may be formed of a different metal. In some instances, the medical implant may be subjected to significant temperature variations during manufacturing and/or use of the implant, and the thermal expansion properties of the two dissimilar metals may allow the radiopaque marker to become dislodged from the structural member. In the case of vascular implants, such dislodging of the radiopaque marker undesirably may create an embolus in the subject's blood stream.

According to existing techniques, a radiopaque marker may be secured to a structural member of a medical implant by welding or by mechanically pressing the radiopaque marker such that the marker is deformed to assume a shape that corresponds to a predefined shape of an opening or recess of the structural member. Welding of the radiopaque marker to the structural member may produce material oxides or other negative side effects from the welding, which can be detrimental to the implant and/or harmful to the subject. Although mechanically pressing the radiopaque marker within the opening or recess of the structural member may avoid the issues caused by welding, such an approach may not produce a secure bond between the marker and the structural member. Mechanical pressing techniques generally may rely on an interference fit for retaining the radiopaque marker within the opening or recess of the structural member. As noted above, certain medical implants may be exposed to extreme temperatures or other environmental conditions, for example during manufacturing of the implant and/or loading of the implant onto or within a delivery system, which may be detrimental to the security of the connection between the radiopaque marker and the structural member.

A need therefore exists for improved medical implants with structural members having features for retaining radiopaque markers and related methods for fabricating such medical implants, which may overcome one or more of the above-mentioned limitations associated with existing techniques for securing a radiopaque marker to a structural member of an implant.

SUMMARY OF THE DISCLOSURE

The present disclosure provides medical implants and related methods for fabricating medical implant implants. In one aspect, a medical implant is provided. In one embodiment, the medical implant may include a structural member and a radiopaque marker. The structural member may include a first surface, a second surface disposed opposite the first surface, an opening extending from the first surface to the second surface and defining a central axis, and a plurality of barbs extending into the opening toward the central axis. The barbs may be spaced apart from one another and spaced apart from each of the first surface and the second surface. The radiopaque marker may be disposed within the opening.

In some embodiments, the first surface and the second surface may be planar surfaces, the second surface may extend parallel to the first surface, and the central axis may extend perpendicular to each of the first surface and the second surface. In some embodiments, the first surface and the second surface may be partial-cylindrical surfaces defining a longitudinal axis of the medical implant, and the central axis may extend perpendicular to the longitudinal axis. In some embodiments, the first surface may be an external surface of the medical implant, and the second surface may be an internal surface of the medical implant.

In some embodiments, the opening may be defined by a first curved surface extending from the first surface to the second surface, a second curved surface extending from the first surface to the second surface, a first planar surface disposed between the first curved surface and the second curved surface, and a second planar surface disposed between the first curved surface and the second curved surface. In some embodiments, the plurality of barbs may include a first barb disposed on the first planar surface and a second barb disposed on the second planar surface, and each of the first curved surface and the second curved surface may be devoid of barbs. In some embodiments, the opening may be defined by a first curved surface extending from the first surface to the barbs, and a second curved surface extending from the second surface to the barbs. In some embodiments, each of the first curved surface and the second curved surface may be devoid of barbs.

In some embodiments, each of the barbs may include a first end, a second end disposed opposite the first end in a direction from the first surface toward the second surface, a radially inner surface disposed between the first end and the second end and angled relative to the central axis, and an end surface disposed at the first end or the second end. The radially inner surface and the central axis may define an acute angle therebetween, and the end surface may extend perpendicular to the central axis. In some embodiments, each of the barbs also may include a first lateral side surface disposed between the first end and the second end, and a second lateral side surface disposed between the first end and the second end. The first lateral side surface may extend parallel to the central axis, and the second lateral side surface may extend parallel to the central axis.

In some embodiments, each of the barbs may include a first end, a second end disposed opposite the first end in a direction from the first surface toward the second surface, a first radially inner surface disposed between the first end and the second end and angled relative to the central axis in a first orientation, a second radially inner surface disposed between the first end and the second end and angled relative to the central axis in a second orientation opposite the first orientation, a first end surface disposed at the first end, and a second end surface disposed at the second end. The first radially inner surface and the central axis may define a first acute angle therebetween, the second radially inner surface and the central axis may define a second acute angle therebetween, the first end surface may extend perpendicular to the central axis, and the second end surface may extend perpendicular to the central axis. In some embodiments, each of the barbs also may include a first lateral side surface disposed between the first end and the second end, and a second lateral side surface disposed between the first end and the second end. The first lateral side surface may extend parallel to the central axis, and the second lateral side surface may extend parallel to the central axis.

In some embodiments, each of the barbs may include a first end and a second end disposed opposite the first end in a direction from the first surface toward the second surface, and each of the barbs may have a height from the first end to the second end that is less than each of a first distance from the first end to the first surface and a second distance from the second end to the second surface. In some embodiments, the plurality of barbs may include a first barb and a second barb disposed opposite the first barb with respect to the central axis. In some embodiments, the plurality of barbs may include three or more barbs arranged in a circumferential array around the central axis. In some embodiments, the radiopaque marker may fill the opening. In some embodiments, the medical implant may be a stent. In some embodiments, the opening may be an eyelet of the stent.

In another aspect, a medical implant is provided. In one embodiment, the medical implant may include a structural member and a radiopaque marker. The structural member may include a first surface, a second surface disposed opposite the first surface, an opening extending from the first surface to the second surface and defining a central axis, and a plurality of barbs extending into the opening toward the central axis. The barbs may be spaced apart from one another. Each of the barbs may include a first end, a second end disposed opposite the first end in a direction from the first surface toward the second surface, a radially inner surface disposed between the first end and the second end and angled relative to the central axis, and an end surface disposed at the first end or the second end. The radially inner surface and the central axis may define an acute angle therebetween, and the end surface may extend perpendicular to the central axis. The radiopaque marker may be disposed within the opening.

In still another aspect, a medical implant is provided. In one embodiment, the medical implant may include a structural member and a radiopaque marker. The structural member may include a first surface, a second surface disposed opposite the first surface, an opening extending from the first surface to the second surface and defining a central axis, a first barb, and a second barb. The opening may be defined by a first curved surface extending from the first surface to the second surface, a second curved surface extending from the first surface to the second surface, a first planar surface disposed between the first curved surface and the second curved surface, and a second planar surface disposed between the first curved surface and the second curved surface. The first barb may be disposed on the first planar surface and extend into the opening toward the central axis, and the second barb may be disposed on the second planar surface and extend into the opening toward the central axis.

These and other aspects and improvements of the present disclosure will become apparent to one of ordinary skill in the art upon review of the following detailed description when taken in conjunction with the several drawings and the appended claims.

BRIEF DESCRIPTION OF THE DRAWINGS

FIG. 1A is a top view of a portion of an example medical implant in accordance with one or more embodiments of the disclosure, the medical implant including a structural member having an opening defined therein and a plurality of barbs.

FIG. 1B is a detailed top view of a portion of the medical implant of FIG. 1A, showing the opening and the barbs.

FIG. 1C is a cross-sectional plan view of a portion of the medical implant of FIG. 1A, with the cross-section taken along plane 1C-1C of FIG. 1A.

FIG. 1D is a cross-sectional plan view of a portion of the medical implant of FIG. 1A, similar to the cross-section of FIG. 1C.

FIG. 1E is a detailed cross-sectional plan view of a portion of the medical implant of FIG. 1A, similar to the cross-section of FIG. 1C, showing the opening and the barbs.

FIG. 1F is a detailed cross-sectional plan view of a portion of the medical implant of FIG. 1A, similar to the cross-section of FIG. 1C, showing the opening, the barbs, and a radiopaque marker disposed within the opening.

FIG. 3A is a top view of a portion of an example medical implant in accordance with one or more embodiments of the disclosure, the medical implant including a structural member having an opening defined therein and a plurality of barbs.

FIG. 3B is a detailed top view of a portion of the medical implant of FIG. 3A, showing the opening and the barbs.

FIG. 3C is a cross-sectional plan view of a portion of the medical implant of FIG. 3A, with the cross-section taken along plane 3C-3C of FIG. 3A.

FIG. 3D is a cross-sectional plan view of a portion of the medical implant of FIG. 3A, similar to the cross-section of FIG. 3C.

FIG. 3E is a detailed cross-sectional plan view of a portion of the medical implant of FIG. 3A, similar to the cross-section of FIG. 3C, showing the opening and the barbs.

FIG. 3F is a detailed cross-sectional plan view of a portion of the medical implant of FIG. 3A, similar to the cross-section of FIG. 3C, showing the opening, the barbs, and a radiopaque marker disposed within the opening.

Figure 2A:
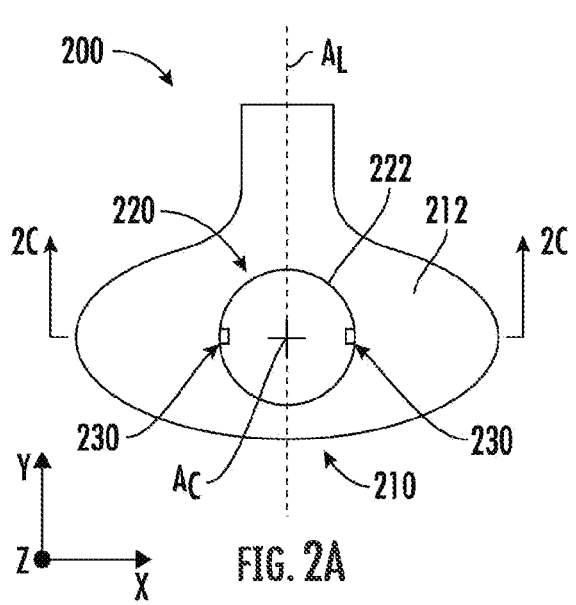
FIG. 2A is a top view of a portion of an example medical implant in accordance with one or more embodiments of the disclosure, the medical implant including a structural member having an opening defined therein and a plurality of barbs.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Embodiments of medical implants with structural members having barbs (which also may be referred to as "projections" or "protrusions") for retaining radiopaque markers (which also may be referred to as "radiopaque elements," "radiopaque members," "radiopaque marker inserts," "radiopaque inserts," or "marker inserts") and related methods for fabricating such medical implants are provided herein. In some instances, the medical implants may be stents, such as intravascular stents, although the medical implants may be any type of implant having one or more radiopaque markers connected to one or more structural members of the implant. The radiopaque markers may be provided to facilitate visualization, via X-ray imaging and the like, of the implant relative to the anatomy of a subject during and/or after implantation. The radiopaque markers may be formed of a precious or other rare earth metal, such as gold and the like, while the structural members may be formed of a different metal.

The medical implants provided herein generally may include a structural member and a radiopaque marker connected to the structural member. The structural member may include a first surface, a second surface disposed opposite the first surface, and an opening extending from the first surface to the second surface and defining a central axis. The radiopaque marker may be disposed within the opening. The structural member may include a plurality of barbs extending into the opening toward the central axis and configured to facilitate retention of the radiopaque marker. In other words, the barbs of the structural member may cooperate with the radiopaque marker to retain the marker within the opening, inhibiting the marker from becoming disconnected from the structural member. As described herein, various geometries of the openings and the barbs may be used. In some embodiments, the opening may be defined by a pair of curved surfaces, with a first curved surface extending from the first surface to the barbs, and a second curved surface extending from the second surface to the barbs. In other words, the barbs may be positioned between the first curved surface and the second curved surface in a direction from the first surface to the second surface. In some embodiments, the first curved surface and the second curved surface may be cylindrical surfaces. In some embodiments, the first curved surface and the second curved surface may be frustoconical surfaces. The opening also may be defined by two or more additional curved surfaces extending circumferentially between adjacent pairs of the barbs. In some embodiments, the additional curved surfaces may be partial-cylindrical surfaces. In some embodiments, the additional curved surfaces may be partial-frustoconical surfaces. In some embodiments, the opening may be defined by two or more curved surfaces extending from the first surface to the second surface, and two or more planar surfaces, with each planar surface being disposed between two of the curved surfaces in the circumferential direction. In such embodiments, the barbs may be disposed on the planar surfaces, and the curved surfaces may be devoid of barbs. In some embodiments, the curved surfaces may be partial-cylindrical surfaces. In some embodiments, the curved surfaces may be partial-frustoconical surfaces. Various shapes and configurations of the opening may be used in other embodiments.

As discussed above, existing techniques for securing a radiopaque marker to a structural member of a medical implant may have certain limitations. In some instances, a radiopaque marker may be welded to a structural member of a medical implant. However, such welding may produce material oxides or other negative side effects from the welding, which can be detrimental to the implant and/or harmful to the subject. In some instances, a radiopaque marker may be mechanically pressed such that the marker is deformed to assume a shape that corresponds to a predefined shape of an opening of a structural member of a medical implant. For example, the opening may have a cylindrical or frustoconical shape, and the radiopaque marker may be placed within the opening and deformed from a spherical shape to a cylindrical or frustoconical shape to match the opening. In this manner, an interference fit may be provided for retaining the radiopaque marker within the opening. Although pressing and deforming the radiopaque marker may avoid the issues caused by welding, such an approach may not produce a secure bond between the marker and the structural member. Certain types of medical implants may be exposed to extreme temperatures or other environmental conditions, for example during manufacturing of the implant, loading of the implant onto or within a delivery system, and/or use of the implant. In some instances, such temperatures may be detrimental to the security of the connection between the radiopaque marker and the structural member. For example, the thermal expansion properties of the metal used for the radiopaque marker and the different metal used for the structural member may compromise the interference-fit connection, allowing the marker to become dislodged from the structural member. Such separation of the radiopaque marker from the structural member may be problematic for various types of medical implants, raising significant concerns with respect to the subject's safety. For example, in the case of vascular implants, a dislodged radiopaque marker undesirably may create an embolus in the subject's blood stream.

The medical implants and related methods provided herein advantageously may overcome one or more of the limitations associated with existing techniques for securing a radiopaque marker to a structural member of a medical implant. Notably, the disclosed medical implants do not rely on welds for securing a radiopaque marker to a structural member, and thus the implants avoid the welding-related problems mentioned above. As described herein, the medical implants include a structural member having an opening, and a radiopaque marker that is positioned and deformed within the opening to assume a shape corresponding to a shape of the opening. However, in contrast to existing techniques that utilize a conventional cylindrical or frustoconical opening, the implants provided herein utilize openings and a plurality of barbs extending into the openings and configured to facilitate retention of the radiopaque marker. As described below, various geometries and arrangements of the barbs may be used such that the resulting connection between the radiopaque marker and the structural member may provide enhanced retention of the marker, allowing the medical implant to withstand extreme temperatures or other environmental conditions without compromising the integrity of the connection.

In some embodiments, each of the barbs may include a first end, a second end disposed opposite the first end in a direction from the first surface toward the second surface, a radially inner surface disposed between the first end and the second end and angled relative to the central axis, and an end surface disposed at the first end or the second end. The radially inner surface and the central axis may define an acute angle therebetween, and the end surface may extend transverse, such as perpendicular or substantially perpendicular, to the central axis. In such embodiments, the end surface oriented transverse to the central axis may enhance retention of the radiopaque marker in a predefined direction. Specifically, when the end surface is disposed at the first end, the interface between the end surface and the deformed radiopaque marker may inhibit dislodgment of the marker in the direction from the first surface toward the second surface. Conversely, when the end surface is disposed at the second end, the interface between the end surface and the deformed radiopaque marker may inhibit dislodgment of the marker in the direction from the second surface toward the first surface.

In some embodiments, each of the barbs may have a symmetrical shape configured to enhance retention of the radiopaque marker in two predefined directions opposite one another. For example, each of the barbs may include a first end, a second end disposed opposite the first end in a direction from the first surface toward the second surface, a first radially inner surface disposed between the first end and the second end and angled relative to the central axis in a first orientation, a second radially inner surface disposed between the first end and the second end and angled relative to the central axis in a second orientation opposite the first orientation, a first end surface disposed at the first end, and a second end surface disposed at the second end. The first radially inner surface and the central axis may define a first acute angle therebetween, the second radially inner surface and the central axis may define a second acute angle therebetween, the first end surface may extend transverse, such as perpendicular or substantially perpendicular, to the central axis, and the second end surface may extend transverse, such as perpendicular or substantially perpendicular, to the central axis. In such embodiments, the interface between the first end surface and the deformed radiopaque marker may inhibit dislodgment of the marker in the direction from the first surface toward the second surface, while the interface between the second end surface and the deformed radiopaque marker may inhibit dislodgment of the marker in the direction from the second surface toward the first surface.

Still other benefits and advantages of the medical implants and fabrication methods provided herein over existing technology for securing a radiopaque marker to a structural member of an implant will be appreciated by those of ordinary skill in the art from the following description and the appended drawings.

Defined Terms

As used herein, the term "defined by," when referring to an opening being "defined by" one or more surfaces and/or edges, means that the one or more surfaces and/or edges define(s) at least a portion of the opening. In this manner, the term "defined by" is not exclusive, as use of the term leaves open the possibility that one or more additional surfaces and/or edges may define one or more additional portions of the opening. As used herein, the term "defined entirely by," when referring to an opening being "defined entirely by" one or more surfaces and/or edges, means that the one or more surfaces and/or edges define(s) the entirety of the opening. In this manner, the term "defined entirely by" is exclusive with respect to additional surfaces or edges.

As used herein, the term "partial-cylindrical surface" means a curved surface that has a constant radius of curvature about a central axis but constitutes less than a complete cylindrical surface. As used herein, the term "central axis," when referring to a partial-cylindrical surface defining a "central axis," means the axis from which the constant radius of curvature of the partial-cylindrical surface extends.

As used herein, the term "partial-frustoconical surface" means a curved surface that has a constant radius of curvature about a central axis in a circumferential direction and a linearly variable radius of curvature in an axial direction but constitutes less than a complete frustoconical surface. As used herein, the term "central axis," when referring to a partial-frustoconical surface defining a "central axis," means the axis from which the constant radius of curvature and the linearly variable radius of curvature of the partial-frustoconical surface extends.

As used herein, the term "substantially perpendicular," when referring to a relationship between two features, means that the features are perpendicular to one another or within 5 degrees of being perpendicular to one another.

As used herein, the term "substantially parallel," when referring to a relationship between two features, means that the features are parallel to one another or within 5 degrees of being parallel to one another.

As used herein, a recitation of a numerical range is inclusive of the bounds used to define the range. For example, a "range from X to Y" is inclusive of "X" and "Y."

Example Embodiments of Medical Implants

Referring now to FIGS. 1A-1F, a portion of an example medical implant 100 (which also may be referred to as a "medical device" or simply an "implant") is depicted. Respective X, Y, and Z axes are shown in the figures to facilitate description of certain features of the illustrated embodiment and relationships therebetween. In some embodiments, the medical implant 100 may be a stent, such as an intravascular stent, although various other configurations of the implant 100 may be used in other embodiments. In some embodiments, the medical implant 100 may be formed as an elongated structure having a longitudinal axis $A_L$ (extending in the Y direction). For example, when the implant 100 is a stent, the longitudinal axis $A_L$ may be the axis with respect to which the stent radially expands. The implant 100 may include a structural member 110 (which also may be referred to as a "base member" or a "base") and a radiopaque marker 160 (which also may be referred to as a "radiopaque element," a "radiopaque member," a "radiopaque marker insert," a "radiopaque insert," or a "marker insert") that is fixedly connected to the structural member 110. In other words, after assembly, the radiopaque marker 160 is not intended to be removed from the structural member 110. In some embodiments, the structural member 110 may be a beam of the medical implant 100. For example, when the implant 100 is a stent, the structural member 110 may be a beam of the stent, such as a strut of the stent.

As shown, the structural member 110 may have a first surface 112, a second surface 114 disposed opposite the first surface 112 (in the Z direction), and an opening 120 (which also may be referred to as a "hole," a "through-hole," or an "aperture") that extends from the first surface 112 to the second surface 114 (in the Z direction). The structural member 110 may have a wall thickness between the first surface 112 and the second surface 114 (in the Z direction). In some embodiments, as shown, the structural member 110 may have a constant wall thickness between the first surface 112 and the second surface 114. In some embodiments, as shown in FIG. 1C, the first surface 112 and the second surface 114 may be planar surfaces, and the second surface 114 may extend parallel, or substantially parallel, to the first surface 112. In some embodiments, as shown in FIG. 1D, the first surface 112 and the second surface 114 may be curved surfaces. For such embodiments, references herein to a feature (e.g., an axis, a surface, etc.) extending "perpendicular" to the first surface 112 and/or the second surface 114 mean that the feature extends perpendicular to a tangent of the curved surface at a location where the feature intersects the first surface 112 and/or the second surface 114. In some embodiments, the first surface 112 and the second surface 114 may be partial-cylindrical surfaces that define the longitudinal axis $A_L$ of the implant 100. In some embodiments, the first surface 112 may be an external surface of the implant 100, and the second surface 114 may be an internal surface of the implant 100. For example, when the implant 100 is a stent, the first surface 112 may be a radially outer surface of the implant 100, and the second surface 114 may be a radially inner surface of the implant 100. The opening 120 may have a central axis $A_C$ extending (in the Z direction) through a center of the opening 120. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 112 and the second surface 114. In some embodiments, when the implant 100 is a stent, the opening 120 may be an eyelet of the stent. In some embodiments, as shown in FIG. 1F, the radiopaque marker 160 may fill the opening 120. In some embodiments, the radiopaque marker 160 may be flush with each of the first surface 112 and the second surface 114, as shown.

The opening 120 may be defined by a plurality of surfaces and/or edges. According to the illustrated embodiment, the opening 120 may be defined by a first curved surface 122 extending from the first surface 112 toward the second surface 114 and a second curved surface 124 extending from the second surface 114 toward the first surface 112. In some embodiments, as shown in FIG. 1C, the first curved surface 122 and the second curved surface 124 may be cylindrical surfaces. In some embodiments, as shown in FIG. 1D, the first curved surface 122 and the second curved surface 124 may be frustoconical surfaces. As shown, the first curved surface 122 and the second curved surface 124 may define respective central axes that are coaxial with the central axis $A_C$ of the opening 120. In other words, the central axis $A_C$ may be defined by the first curved surface 122 and the second curved surface 124. The opening 120 also may be defined by two or more additional curved surfaces disposed circumferentially between adjacent pairs of barbs 130, as described further below.

As shown in FIGS. 1A-1F, the structural member 110 may include a plurality of barbs 130 extending into the opening 120 toward the central axis $A_C$ (in the radial direction with respect to the central axis $A_C$). Although two (2) barbs 130 are shown in the illustrated embodiment, three (3), four (4), five (5), six (6), or more barbs 130 may be used in other embodiments. As shown, the pair of barbs 130 may be spaced apart from one another in the circumferential direction and disposed opposite one another with respect to the central axis $A_C$, although other arrangements of the pair of barbs 130 may be used. In embodiments in which three or more barbs 130 are provided, the barbs 130 may be arranged in a circumferential array around the central axis $A_C$. In such embodiments, the barbs 130 may be equally spaced apart from one another or spaced apart from one another at unequal spacings in the circumferential direction around the central axis $A_C$. The circumferential spacing of the barbs 130 may result in respective additional curved surfaces disposed between adjacent pairs of the barbs 130 (in the circumferential direction around the central axis $A_C$) and between the first curved surface 122 and the second curved surface 124 (in the Z direction), with the additional curved surfaces further defining the opening 120. In some embodiments, as shown in FIG. 1C, the additional curved surfaces may be partial-cylindrical surfaces. In some embodiments, as shown in FIG. 1D, the additional curved surfaces may be partial-frustoconical surfaces. As shown, the barbs 130 may be spaced apart from each of the first surface 112 and the second surface 114. Specifically, the barbs 130 may be spaced apart from the first surface 112 by the first curved surface 122 and may be spaced apart from the second surface 114 by the second curved surface 124. In this manner, the first curved surface 122 may extend from the first surface 112 to the barbs 130, and the second curved surface 124 may extend from the second surface 114 to the barbs 130. In some embodiments, as shown, the first curved surface 122 and the second curved surface 124 may be devoid of barbs 130.

As shown in detail in FIGS. 1B and 1E, each of the barbs 130 may have a first end 132, a second end 134, a first lateral side 136, a second lateral side 138, and a radially inner side 140. The second end 134 may be disposed opposite the first end 132 in the direction from the first surface 112 toward the second surface 114 (the "−" Z direction). In this manner, the first end 132 may be disposed closer to the first surface 112, and the second end 134 may be disposed closer to the second surface 114. In some embodiments, as shown, each of the barbs 130 may have a height from the first end 132 to the second end 134 (in the Z direction) that is less than each of a first distance from the first end 132 to the first surface 112 (in the Z direction) and a second distance from the second end 134 to the second surface 114 (in the Z direction). Other relative sizes and configurations of the barbs 130, the first curved surface 122, and the second curved surface 124 may be used in other embodiments.

Each of the barbs 130 may include an end surface 144, a first lateral side surface 146, a second lateral side surface 148, and a radially inner surface 150. As shown, the end surface 144 may be disposed at the second end 134 of the barb 130 and may be formed as a planar surface extending perpendicular, or substantially perpendicular, to the central axis $A_C$. Although a perpendicular orientation of the end surface 144 is provided in the illustrated embodiment, other orientations transverse to the central axis $A_C$ may be used in other embodiments. As shown, the first lateral side surface 146 may extend along the first lateral side 136 of the barb 130 and be disposed between the first end 132 and the second end 134. In some embodiments, as shown, the first lateral side surface 146 may extend from the first end 132 to the second end 134 and may be formed as a planar surface extending parallel, or substantially parallel, to the central axis $A_C$. In a similar manner, the second lateral side surface 148 may extend along the second lateral side 138 of the barb 130 and be disposed between the first end 132 and the second end 134. In some embodiments, as shown, the second lateral side surface 148 may extend from the first end 132 to the second end 134 and may be formed as a planar surface extending parallel, or substantially parallel, to the central axis $A_C$. In some embodiments, as shown, each of the barbs 130 may have a lateral thickness from the first lateral side surface 146 to the second lateral side surface 148 that is less than the height of the barb 130. As shown, the radially inner surface 150 may extend along the radially inner side 140 of the barb 130 and be disposed between the first end 132 and the second end 134. In some embodiments, as shown, the radially inner surface 150 may extend from the first end 132 to the second end 134 and may be formed as a planar surface that is angled relative to the central axis $A_C$. As shown, the radially inner surface 150 and the central axis $A_C$ may define an acute angle $\alpha$ therebetween. In some embodiments, the acute angle $\alpha$ may be within a range of 5 degrees to 30 degrees, although other values of the acute angle $\alpha$ may be used. Various relative dimensions and configurations of the barbs 130 may be used in accordance with different embodiments.

FIGS. 2A-2F depict a portion of another example medical implant 200 (which also may be referred to as a "medical device" or simply an "implant"). Respective X, Y, and Z axes are shown in the figures to facilitate description of certain features of the illustrated embodiment and relationships therebetween. Certain similarities and differences between the implant 200 and the implant 100 described above will be appreciated from the drawings and the following description. Particular differences relate to the orientation of the barbs with respect to the first surface and the second surface of the structural member. Corresponding reference numbers are used for corresponding features, which generally may be configured in a manner similar to the features described above unless indicated otherwise. In some embodiments, the medical implant 200 may be a stent, such as an intravascular stent, although various other configurations of the implant 200 may be used in other embodiments. In some embodiments, the medical implant 200 may be formed as an elongated structure having a longitudinal axis $A_L$ (extending in the Y direction). For example, when the implant 200 is a stent, the longitudinal axis $A_L$ may be the axis with respect to which the stent radially expands. The implant 200 may include a structural member 210 (which also may be referred to as a "base member" or a "base") and a radiopaque marker 260 (which also may be referred to as a "radiopaque element," a "radiopaque member," a "radiopaque marker insert," a "radiopaque insert," or a "marker insert") that is fixedly connected to the structural member 210. In other words, the radiopaque marker 260 is not intended to be removed from the structural member 210. In some embodiments, the structural member 210 may be a beam of the medical implant 200. For example, when the implant 200 is a stent, the structural member 210 may be a beam of the stent, such as a strut of the stent.

As shown, the structural member 210 may have a first surface 212, a second surface 214 disposed opposite the first surface 212 (in the Z direction), and an opening 220 (which also may be referred to as a "hole," a "through-hole," or an "aperture") that extends from the first surface 212 to the second surface 214 (in the Z direction). The structural member 210 may have a wall thickness between the first surface 212 and the second surface 214 (in the Z direction). In some embodiments, as shown, the structural member 210 may have a constant wall thickness between the first surface 212 and the second surface 214. In some embodiments, as shown in FIG. 2C, the first surface 212 and the second surface 214 may be planar surfaces, and the second surface 214 may extend parallel, or substantially parallel, to the first surface 212. In some embodiments, as shown in FIG. 2D, the first surface 212 and the second surface 214 may be curved surfaces. For such embodiments, references herein to a feature (e.g., an axis, a surface, etc.) extending "perpendicular" to the first surface 212 and/or the second surface 214 mean that the feature extends perpendicular to a tangent of the curved surface at a location where the feature intersects the first surface 212 and/or the second surface 214. In some embodiments, the first surface 212 and the second surface 214 may be partial-cylindrical surfaces that define the longitudinal axis $A_L$ of the implant 200. In some embodiments, the first surface 212 may be an external surface of the implant 200, and the second surface 214 may be an internal surface of the implant 200. For example, when the implant 200 is a stent, the first surface 212 may be a radially outer surface of the implant 200, and the second surface 214 may be a radially inner surface of the implant 200. The opening 220 may have a central axis $A_C$ extending (in the Z direction) through a center of the opening 220. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 212 and the second surface 214. In some embodiments, when the implant 200 is a stent, the opening 220 may be an eyelet of the stent. In some embodiments, as shown in FIG. 2F, the radiopaque marker 260 may fill the opening 220. In some embodiments, the radiopaque marker 260 may be flush with each of the first surface 212 and the second surface 214, as shown.

The opening 220 may be defined by a plurality of surfaces and/or edges. According to the illustrated embodiment, the opening 220 may be defined by a first curved surface 222 extending from the first surface 212 toward the second surface 214 and a second curved surface 224 extending from the second surface 214 toward the first surface 212. In some embodiments, as shown in FIG. 2C, the first curved surface 222 and the second curved surface 224 may be cylindrical surfaces. In some embodiments, as shown in FIG. 2D, the first curved surface 222 and the second curved surface 224 may be frustoconical surfaces. As shown, the first curved surface 222 and the second curved surface 224 may define respective central axes that are coaxial with the central axis $A_C$ of the opening 220. In other words, the central axis $A_C$ may be defined by the first curved surface 222 and the second curved surface 224. The opening 220 also may be defined by two or more additional curved surfaces disposed circumferentially between adjacent pairs of barbs 230, as described further below.

As shown in FIGS. 2A-2F, the structural member 210 may include a plurality of barbs 230 extending into the opening 220 toward the central axis $A_C$ (in the radial direction with respect to the central axis $A_C$). Although two (2) barbs 230 are shown in the illustrated embodiment, three (3), four (4), five (5), six (6), or more barbs 230 may be used in other embodiments. As shown, the pair of barbs 230 may be spaced apart from one another in the circumferential direction and disposed opposite one another with respect to the central axis $A_C$, although other arrangements of the pair of barbs 230 may be used. In embodiments in which three or more barbs 230 are provided, the barbs 230 may be arranged in a circumferential array around the central axis $A_C$. In such embodiments, the barbs 230 may be equally spaced apart from one another or spaced apart from one another at unequal spacings in the circumferential direction around the central axis $A_C$. The circumferential spacing of the barbs 230 may result in respective additional curved surfaces disposed between adjacent pairs of the barbs 230 (in the circumferential direction around the central axis $A_C$) and between the first curved surface 222 and the second curved surface 224 (in the Z direction), with the additional curved surfaces further defining the opening 220. In some embodiments, as shown in FIG. 2C, the additional curved surfaces may be partial-cylindrical surfaces. In some embodiments, as shown in FIG. 2D, the additional curved surfaces may be partial-frustoconical surfaces. As shown, the barbs 230 may be spaced apart from each of the first surface 212 and the second surface 214. Specifically, the barbs 230 may be spaced apart from the first surface 212 by the first curved surface 222 and may be spaced apart from the second surface 214 by the second curved surface 224. In this manner, the first curved surface 222 may extend from the first surface 212 to the barbs 230, and the second curved surface 224 may extend from the second surface 214 to the barbs 230. In some embodiments, as shown, the first curved surface 222 and the second curved surface 224 may be devoid of barbs 230.

Figure 2B:
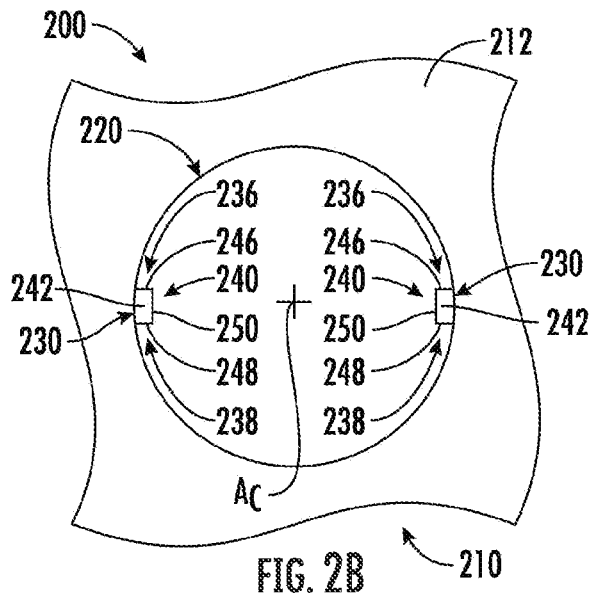
FIG. 2B is a detailed top view of a portion of the medical implant of FIG. 2A, showing the opening and the barbs.
Figure 2C:
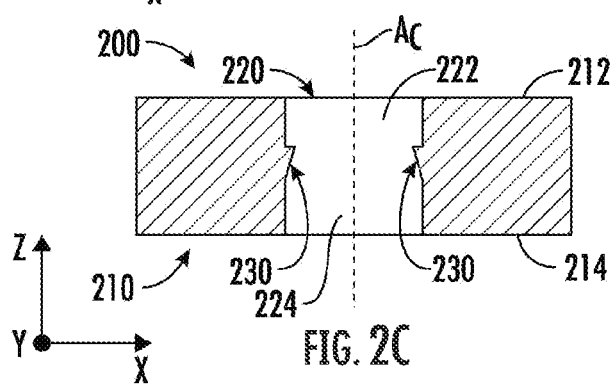
FIG. 2C is a cross-sectional plan view of a portion of the medical implant of FIG. 2A, with the cross-section taken along plane 2C-2C of FIG. 2A.
Figure 2D:
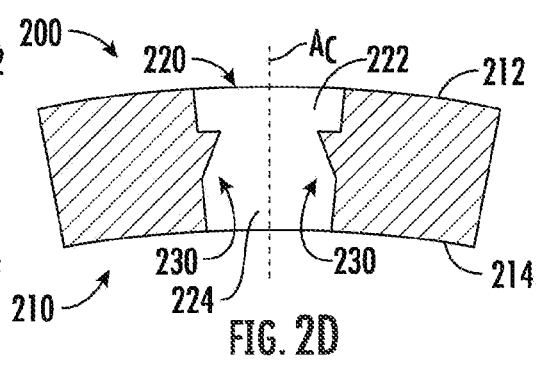
FIG. 2D is a cross-sectional plan view of a portion of the medical implant of FIG. 2A, similar to the cross-section of FIG. 2C.
Figure 2E:
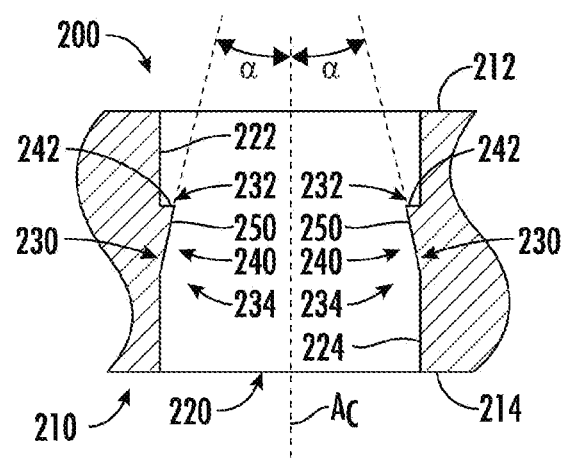
FIG. 2E is a detailed cross-sectional plan view of a portion of the medical implant of FIG. 2A, similar to the cross-section of FIG. 2C, showing the opening and the barbs.
Figure 2F:
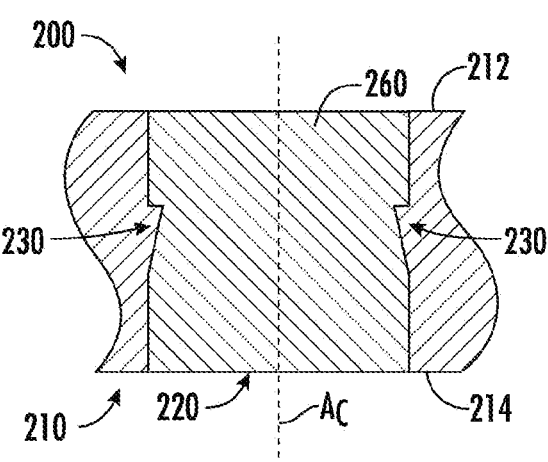
FIG. 2F is a detailed cross-sectional plan view of a portion of the medical implant of FIG. 2A, similar to the cross-section of FIG. 2C, showing the opening, the barbs, and a radiopaque marker disposed within the opening.

As shown in detail in FIGS. 2B and 2E, each of the barbs 230 may have a first end 232, a second end 234, a first lateral side 236, a second lateral side 238, and a radially inner side 240. The second end 234 may be disposed opposite the first end 232 in the direction from the first surface 212 toward the second surface 214 (the "−" Z direction). In this manner, the first end 232 may be disposed closer to the first surface 212, and the second end 234 may be disposed closer to the second surface 214. In some embodiments, as shown, each of the barbs 230 may have a height from the first end 232 to the second end 234 (in the Z direction) that is less than each of a first distance from the first end 232 to the first surface 212 (in the Z direction) and a second distance from the second end 234 to the second surface 214 (in the Z direction). Other relative sizes and configurations of the barbs 230, the first curved surface 222, and the second curved surface 224 may be used in other embodiments.

Each of the barbs 230 may include an end surface 242, a first lateral side surface 246, a second lateral side surface 248, and a radially inner surface 250. As shown, the end surface 242 may be disposed at the first end 232 of the barb 230 and may be formed as a planar surface extending perpendicular, or substantially perpendicular, to the central axis $A_C$. Although a perpendicular orientation of the end surface 242 is provided in the illustrated embodiment, other orientations transverse to the central axis $A_C$ may be used in other embodiments. As shown, the first lateral side surface 246 may extend along the first lateral side 236 of the barb 230 and be disposed between the first end 232 and the second end 234. In some embodiments, as shown, the first lateral side surface 246 may extend from the first end 232 to the second end 234 and may be formed as a planar surface extending parallel, or substantially parallel, to the central axis $A_C$. In a similar manner, the second lateral side surface 248 may extend along the second lateral side 238 of the barb 230 and be disposed between the first end 232 and the second end 234. In some embodiments, as shown, the second lateral side surface 248 may extend from the first end 232 to the second end 234 and may be formed as a planar surface extending parallel, or substantially parallel, to the central axis $A_C$. In some embodiments, as shown, each of the barbs 230 may have a lateral thickness from the first lateral side surface 246 to the second lateral side surface 248 that is less than the height of the barb 230. As shown, the radially inner surface 250 may extend along the radially inner side 240 of the barb 230 and be disposed between the first end 232 and the second end 234. In some embodiments, as shown, the radially inner surface 250 may extend from the first end 232 to the second end 234 and may be formed as a planar surface that is angled relative to the central axis $A_C$. As shown, the radially inner surface 250 and the central axis $A_C$ may define an acute angle α therebetween. In some embodiments, the acute angle α may be within a range of 5 degrees to 30 degrees, although other values of the acute angle α may be used. Various relative dimensions and configurations of the barbs 230 may be used in accordance with different embodiments.

FIGS. 3A-3F depict a portion of another example medical implant 300 (which also may be referred to as a "medical device" or simply an "implant"). Respective X, Y, and Z axes are shown in the figures to facilitate description of certain features of the illustrated embodiment and relationships therebetween. Certain similarities and differences between the implant 300 and the implants 100, 200 described above will be appreciated from the drawings and the following description. Particular differences relate to the shape of the barbs and the presence of multiple end surfaces thereof. Corresponding reference numbers are used for corresponding features, which generally may be configured in a manner similar to the features described above unless indicated otherwise. In some embodiments, the medical implant 300 may be a stent, such as an intravascular stent, although various other configurations of the implant 300 may be used in other embodiments. In some embodiments, the medical implant 300 may be formed as an elongated structure having a longitudinal axis $A_L$ (extending in the Y direction). For example, when the implant 300 is a stent, the longitudinal axis $A_L$ may be the axis with respect to which the stent radially expands. The implant 300 may include a structural member 310 (which also may be referred to as a "base member" or a "base") and a radiopaque marker 360 (which also may be referred to as a "radiopaque element," a "radiopaque member," a "radiopaque marker insert," a "radiopaque insert," or a "marker insert") that is fixedly connected to the structural member 310. In other words, the radiopaque marker 360 is not intended to be removed from the structural member 310. In some embodiments, the structural member 310 may be a beam of the medical implant 300. For example, when the implant 300 is a stent, the structural member 310 may be a beam of the stent, such as a strut of the stent.

As shown, the structural member 310 may have a first surface 312, a second surface 314 disposed opposite the first surface 312 (in the Z direction), and an opening 320 (which also may be referred to as a "hole," a "through-hole," or an "aperture") that extends from the first surface 312 to the second surface 314 (in the Z direction). The structural member 310 may have a wall thickness between the first surface 312 and the second surface 314 (in the Z direction). In some embodiments, as shown, the structural member 310 may have a constant wall thickness between the first surface 312 and the second surface 314. In some embodiments, as shown in FIG. 3C, the first surface 312 and the second surface 314 may be planar surfaces, and the second surface 314 may extend parallel, or substantially parallel, to the first surface 312. In some embodiments, as shown in FIG. 3D, the first surface 312 and the second surface 314 may be curved surfaces. For such embodiments, references herein to a feature (e.g., an axis, a surface, etc.) extending "perpendicular" to the first surface 312 and/or the second surface 314 mean that the feature extends perpendicular to a tangent of the curved surface at a location where the feature intersects the first surface 312 and/or the second surface 314. In some embodiments, the first surface 312 and the second surface 314 may be partial-cylindrical surfaces that define the longitudinal axis $A_L$ of the implant 300. In some embodiments, the first surface 312 may be an external surface of the implant 300, and the second surface 314 may be an internal surface of the implant 300. For example, when the implant 300 is a stent, the first surface 312 may be a radially outer surface of the implant 300, and the second surface 314 may be a radially inner surface of the implant 300. The opening 320 may have a central axis $A_C$ extending (in the Z direction) through a center of the opening 320. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 312 and the second surface 314. In some embodiments, when the implant 300 is a stent, the opening 320 may be an eyelet of the stent. In some embodiments, as shown in FIG. 3F, the radiopaque marker 360 may fill the opening 320. In some embodiments, the radiopaque marker 360 may be flush with each of the first surface 312 and the second surface 314, as shown.

The opening 320 may be defined by a plurality of surfaces and/or edges. According to the illustrated embodiment, the opening 320 may be defined by a first curved surface 322 extending from the first surface 312 toward the second surface 314 and a second curved surface 324 extending from the second surface 314 toward the first surface 312. In some embodiments, as shown in FIG. 3C, the first curved surface 322 and the second curved surface 324 may be cylindrical surfaces. In some embodiments, as shown in FIG. 3D, the first curved surface 322 and the second curved surface 324 may be frustoconical surfaces. As shown, the first curved surface 322 and the second curved surface 324 may define respective central axes that are coaxial with the central axis $A_C$ of the opening 320. In other words, the central axis $A_C$ may be defined by the first curved surface 322 and the second curved surface 324. The opening 320 also may be defined by two or more additional curved surfaces disposed circumferentially between adjacent pairs of barbs 330, as described further below.

As shown in FIGS. 3A-3F, the structural member 310 may include a plurality of barbs 330 extending into the opening 320 toward the central axis $A_C$ (in the radial direction with respect to the central axis $A_C$). Although two (2) barbs 330 are shown in the illustrated embodiment, three (3), four (4), five (5), six (6), or more barbs 330 may be used in other embodiments. As shown, the pair of barbs 330 may be spaced apart from one another in the circumferential direction and disposed opposite one another with respect to the central axis $A_C$, although other arrangements of the pair of barbs 330 may be used. In embodiments in which three or more barbs 330 are provided, the barbs 330 may be arranged in a circumferential array around the central axis $A_C$. In such embodiments, the barbs 330 may be equally spaced apart from one another or spaced apart from one another at unequal spacings in the circumferential direction around the central axis $A_C$. The circumferential spacing of the barbs 330 may result in respective additional curved surfaces disposed between adjacent pairs of the barbs 330 (in the circumferential direction around the central axis $A_C$) and between the first curved surface 322 and the second curved surface 324 (in the Z direction), with the additional curved surfaces further defining the opening 320. In some embodiments, as shown in FIG. 3C, the additional curved surfaces may be partial-cylindrical surfaces. In some embodiments, as shown in FIG. 3D, the additional curved surfaces may be partial-frustoconical surfaces. As shown, the barbs 330 may be spaced apart from each of the first surface 312 and the second surface 314. Specifically, the barbs 330 may be spaced apart from the first surface 312 by the first cylindrical surface 322 and may be spaced apart from the second surface 314 by the second cylindrical surface 324. In this manner, the first cylindrical surface 322 may extend from the first surface 312 to the barbs 330, and the second cylindrical surface 324 may extend from the second surface 314 to the barbs 330. In some embodiments, as shown, the first cylindrical surface 322 and the second cylindrical surface 324 may be devoid of barbs 330.

As shown in detail in FIGS. 3B and 3E, each of the barbs 330 may have a first end 332, a second end 334, a first lateral side 336, a second lateral side 338, and a radially inner side 340. The second end 334 may be disposed opposite the first end 332 in the direction from the first surface 312 toward the second surface 314 (the "−" Z direction). In this manner, the first end 332 may be disposed closer to the first surface 312, and the second end 334 may be disposed closer to the second surface 314. In some embodiments, as shown, each of the barbs 330 may have a height from the first end 332 to the second end 334 (in the Z direction) that is less than each of a first distance from the first end 332 to the first surface 312 (in the Z direction) and a second distance from the second end 334 to the second surface 314 (in the Z direction). Other relative sizes and configurations of the barbs 330, the first curved surface 322, and the second curved surface 324 may be used in other embodiments.

Each of the barbs 330 may include a first end surface 342, a second end surface 344, a first lateral side surface 346, a second lateral side surface 348, a first radially inner surface 350, and a second radially inner surface 352. As shown, the first end surface 342 may be disposed at the first end 332 of the barb 330 and may be formed as a planar surface extending perpendicular, or substantially perpendicular, to the central axis $A_C$. Although a perpendicular orientation of the first end surface 342 is provided in the illustrated embodiment, other orientations transverse to the central axis $A_C$ may be used in other embodiments. In a similar manner, the second end surface 344 may be disposed at the second end 334 of the barb 330 and may be formed as a planar surface extending perpendicular, or substantially perpendicular, to the central axis $A_C$. Although a perpendicular orientation of the second end surface 344 is provided in the illustrated embodiment, other orientations transverse to the central axis $A_C$ may be used in other embodiments. As shown, the first lateral side surface 346 may extend along the first lateral side 336 of the barb 330 and be disposed between the first end 332 and the second end 334. In some embodiments, as shown, the first lateral side surface 346 may extend from the first end 332 to the second end 334 and may be formed as a planar surface extending parallel, or substantially parallel, to the central axis $A_C$. In a similar manner, the second lateral side surface 348 may extend along the second lateral side 338 of the barb 330 and be disposed between the first end 332 and the second end 334. In some embodiments, as shown, the second lateral side surface 348 may extend from the first end 332 to the second end 334 and may be formed as a planar surface extending parallel, or substantially parallel, to the central axis $A_C$. In some embodiments, as shown, each of the barbs 330 may have a lateral thickness from the first lateral side surface 346 to the second lateral side surface 348 that is less than the height of the barb 330. As shown, the first radially inner surface 350 may extend along the radially inner side 340 of the barb 330 and be disposed between the first end 332 and the second end 334. In some embodiments, as shown, the first radially inner surface 350 may extend from the first end 332 to the second radially inner surface 352 and may be formed as a planar surface that is angled relative to the central axis $A_C$ in a first orientation. As shown, the first radially inner surface 350 and the central axis $A_C$ may define a first acute angle $\alpha 1$ therebetween. In some embodiments, the first acute angle $\alpha 1$ may be within a range of 5 degrees to 30 degrees, although other values of the first acute angle $\alpha 1$ may be used. In a similar manner, the second radially inner surface 352 may extend along the radially inner side 340 of the barb 330 and be disposed between the first end 332 and the second end 334. In some embodiments, as shown, the second radially inner surface 352 may extend from the second end 334 to the first radially inner surface 350 and may be formed as a planar surface that is angled relative to the central axis $A_C$ in a second orientation opposite the first orientation. As shown, the second radially inner surface 352 and the central axis $A_C$ may define a second acute angle $\alpha 2$ therebetween. In some embodiments, the second acute angle $\alpha 2$ may be within a range of 5 degrees to 30 degrees, although other values of the second acute angle $\alpha 2$ may be used. In some embodiments, as shown, the second acute angle $\alpha 2$ may be equal to the first acute angle $\alpha 1$, although different values of the second acute angle $\alpha 2$ and the first acute angle $\alpha 1$ may be used in other embodiments. In some embodiments, each of the barbs 330 may have a symmetrical shape. For example, as shown, the shape of each of the barbs 330 may be symmetrical about the intersection between the first radially inner surface 350 and the second radially inner surface 352. Various relative dimensions and configurations of the barbs 330 may be used in accordance with different embodiments.

FIGS. 4A-4F depict a portion of another example medical implant 400 (which also may be referred to as a "medical device" or simply an "implant"). Respective X, Y, and Z axes are shown in the figures to facilitate description of certain features of the illustrated embodiment and relationships therebetween. Certain similarities and differences between the implant 400 and the implant 100 described above will be appreciated from the drawings and the following description. Particular differences relate to the shapes of surfaces defining the opening of the structural member. Corresponding reference numbers are used for corresponding features, which generally may be configured in a manner similar to the features described above unless indicated otherwise. In some embodiments, the medical implant 400 may be a stent, such as an intravascular stent, although various other configurations of the implant 400 may be used in other embodiments. In some embodiments, the medical implant 400 may be formed as an elongated structure having a longitudinal axis $A_L$ (extending in the Y direction). For example, when the implant 400 is a stent, the longitudinal axis $A_L$ may be the axis with respect to which the stent radially expands. The implant 400 may include a structural member 410 (which also may be referred to as a "base member" or a "base") and a radiopaque marker 460 (which also may be referred to as a "radiopaque element," a "radiopaque member," a "radiopaque marker insert," a "radiopaque insert," or a "marker insert") that is fixedly connected to the structural member 410. In other words, the radiopaque marker 460 is not intended to be removed from the structural member 410. In some embodiments, the structural member 410 may be a beam of the medical implant 400. For example, when the implant 400 is a stent, the structural member 410 may be a beam of the stent, such as a strut of the stent.

As shown, the structural member 410 may have a first surface 412, a second surface 414 disposed opposite the first surface 412 (in the Z direction), and an opening 420 (which also may be referred to as a "hole," a "through-hole," or an "aperture") that extends from the first surface 412 to the second surface 414 (in the Z direction). The structural member 410 may have a wall thickness between the first surface 412 and the second surface 414 (in the Z direction). In some embodiments, as shown, the structural member 410 may have a constant wall thickness between the first surface 412 and the second surface 414. In some embodiments, as shown in FIG. 4C, the first surface 412 and the second surface 414 may be planar surfaces, and the second surface 414 may extend parallel, or substantially parallel, to the first surface 412. In some embodiments, as shown in FIG. 4D, the first surface 412 and the second surface 414 may be curved surfaces. For such embodiments, references herein to a feature (e.g., an axis, a surface, etc.) extending "perpendicular" to the first surface 412 and/or the second surface 414 mean that the feature extends perpendicular to a tangent of the curved surface at a location where the feature intersects the first surface 412 and/or the second surface 414. In some embodiments, the first surface 412 and the second surface 414 may be partial-cylindrical surfaces that define the longitudinal axis $A_L$ of the implant 400. In some embodiments, the first surface 412 may be an external surface of the implant 400, and the second surface 414 may be an internal surface of the implant 400. For example, when the implant 400 is a stent, the first surface 412 may be a radially outer surface of the implant 400, and the second surface 414 may be a radially inner surface of the implant 400. The opening 420 may have a central axis $A_C$ extending (in the Z direction) through a center of the opening 420. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 412 and the second surface 414. In some embodiments, when the implant 400 is a stent, the opening 420 may be an eyelet of the stent. In some embodiments, as shown in FIG. 4F, the radiopaque marker 460 may fill the opening 420. In some embodiments, the radiopaque marker 460 may be flush with each of the first surface 412 and the second surface 414, as shown.

The opening 420 may be defined by a plurality of surfaces and/or edges. For example, the opening 420 may be defined by a plurality of curved surfaces and a plurality of planar surfaces. According to the illustrated embodiment, the opening 420 may be defined by a first curved surface 422 extending from the first surface 412 to the second surface 414, a second curved surface 424 extending from the first surface 412 to the second surface 414, a first planar surface 426 extending from the first surface 412 to the second surface 414, and a second planar surface 428 extending from the first surface 412 to the second surface 414. In some embodiments, as shown in FIG. 4C, the first curved surface 422 and the second curved surface 424 may be partial-cylindrical surfaces. In some embodiments, as shown in FIG. 4D, the first curved surface 422 and the second curved surface 424 may be partial-frustoconical surfaces. In some embodiments, as shown in FIG. 4C, each of the first planar surface 426 and the second planar surface 428 may extend parallel, or substantially parallel, to the central axis $A_C$. In some embodiments, as shown in FIG. 4D, each of the first planar surface 426 and the second planar surface 428 may be angled relative to the central axis $A_C$ such that an acute angle is defined between each of the first planar surface 426 and the second planar surface 428 and the central axis $A_C$. The first planar surface 426 may be disposed between the first curved surface 422 and the second curved surface 424 (in the circumferential direction around the central axis $A_C$), and the second planar surface 428 may be disposed between the first curved surface 422 and the second curved surface 424 (in the circumferential direction around the central axis $A_C$). As shown, the first planar surface 426 may extend from the first curved surface 422 to the second curved surface 424 (in the circumferential direction around the central axis $A_C$), and the second planar surface 428 may extend from the first curved surface 422 to the second curved surface 424 (in the circumferential direction around the central axis $A_C$). In this manner, a first edge may be defined at an intersection between the first planar surface 426 and the first curved surface 422, a second edge may be defined at an intersection between the first planar surface 426 and the second curved surface 424, a third edge may be defined at an intersection between the second planar surface 428 and the first curved surface 422, and a fourth edge may be defined at an intersection between the second planar surface 428 and the second curved surface 424, with the edges further defining the opening 420. As shown, the first curved surface 422 and the second curved surface 424 may define respective central axes that are coaxial with the central axis $A_C$ of the opening 420. In other words, the central axis $A_C$ may be defined by the first curved surface 422 and the second curved surface 424. Although two (2) curved surfaces and two (2) planar surfaces are shown in the illustrated embodiment as defining the opening 420, three (3), four (4), five (5), six (6), or more curved surfaces and planar surfaces may be used in other embodiments, with each planar surface being disposed between an adjacent pair of curved surfaces in the circumferential direction.

As shown in FIGS. 4A-4F, the structural member 410 may include a plurality of barbs 430 extending into the opening 420 toward the central axis $A_C$ (in the radial direction with respect to the central axis $A_C$). The barbs 430 may be disposed on the planar surfaces 426, 428. For example, as shown, one of the barbs 430 may be disposed on the first planar surface 426, and another of the barbs 430 may be disposed on the second planar surface 428. Although two (2) barbs 430 are shown in the illustrated embodiment, three (3), four (4), five (5), six (6), or more barbs 430 may be used in other embodiments. In some embodiments, two (2) or more barbs 430 may be disposed on one of the planar surfaces 426, 428. As shown, the pair of barbs 430 may be spaced apart from one another in the circumferential direction and disposed opposite one another with respect to the central axis $A_C$, although other arrangements of the pair of barbs 430 may be used. In embodiments in which three or more barbs 430 are provided, the barbs 430 may be arranged in a circumferential array around the central axis $A_C$. In such embodiments, the barbs 430 may be equally spaced apart from one another or spaced apart from one another at unequal spacings in the circumferential direction around the central axis $A_C$. As shown, the barbs 430 may be spaced apart from each of the first surface 412 and the second surface 414. Specifically, the barbs 430 may be spaced apart from the first surface 412 by a first portion of the respective planar surface 426, 428 and may be spaced apart from the second surface 414 by a second portion of the respective planar surface 426, 428. In some embodiments, as shown, the first curved surface 422 and the second curved surface 424 may be devoid of barbs 430.

Figure 4A:
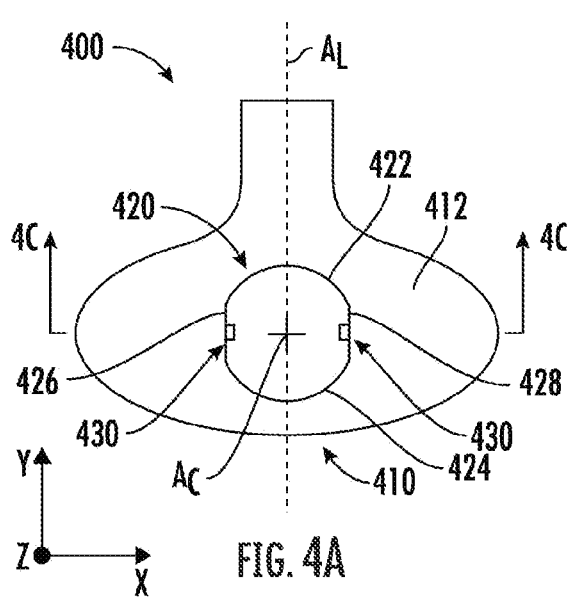
FIG. 4A is a top view of a portion of an example medical implant in accordance with one or more embodiments of the disclosure, the medical implant including a structural member having an opening defined therein and a plurality of barbs.
Figure 4B:
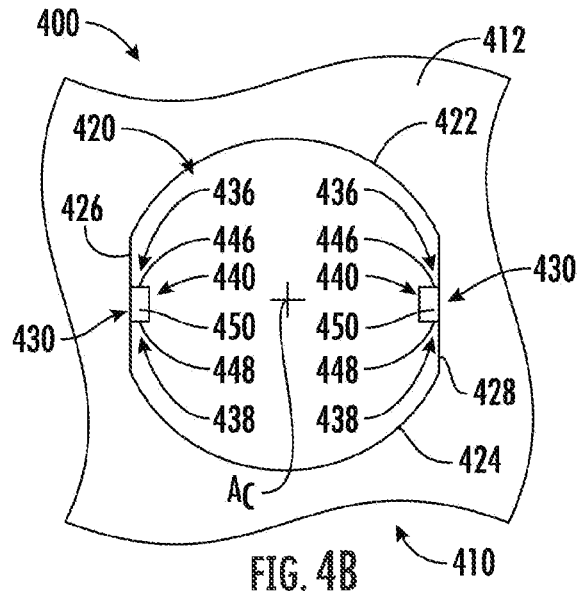
FIG. 4B is a detailed top view of a portion of the medical implant of FIG. 4A, showing the opening and the barbs.
Figure 4C:
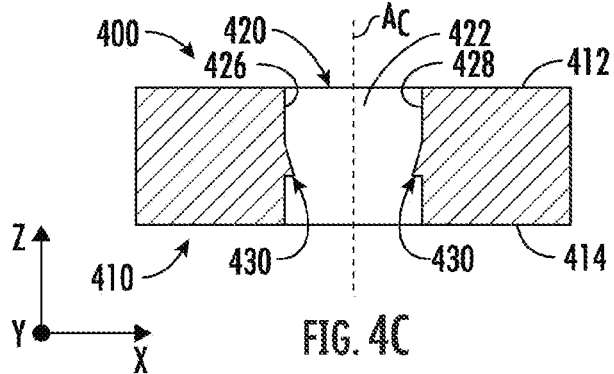
FIG. 4C is a cross-sectional plan view of a portion of the medical implant of FIG. 4A, with the cross-section taken along plane 4C-4C of FIG. 4A.
Figure 4D:
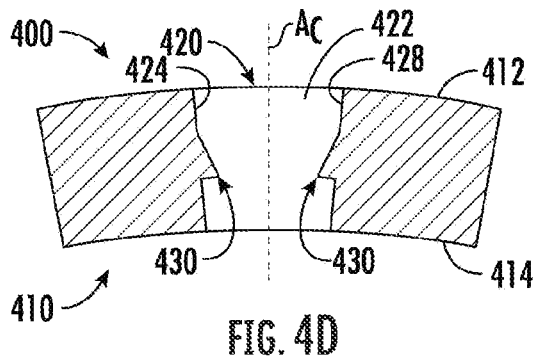
FIG. 4D is a cross-sectional plan view of a portion of the medical implant of FIG. 4A, similar to the cross-section of FIG. 4C.
Figure 4E:
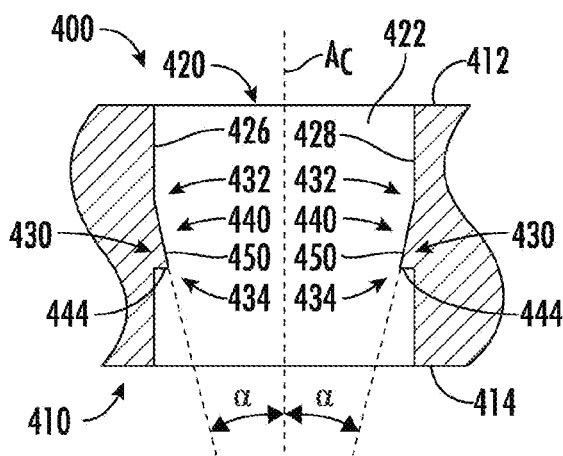
FIG. 4E is a detailed cross-sectional plan view of a portion of the medical implant of FIG. 4A, similar to the cross-section of FIG. 4C, showing the opening and the barbs.
Figure 4F:
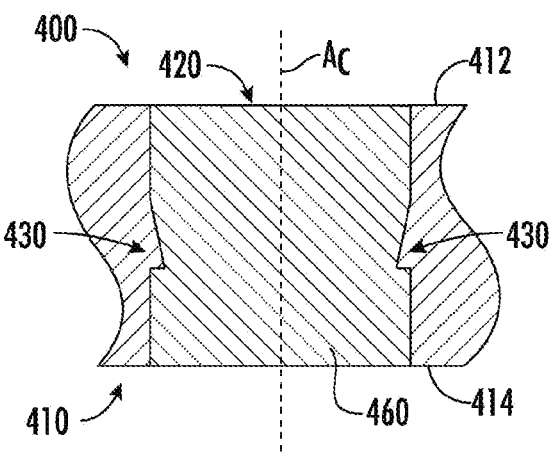
FIG. 4F is a detailed cross-sectional plan view of a portion of the medical implant of FIG. 4A, similar to the cross-section of FIG. 4C, showing the opening, the barbs, and a radiopaque marker disposed within the opening.

As shown in detail in FIGS. 4B and 4E, each of the barbs 430 may have a first end 432, a second end 434, a first lateral side 436, a second lateral side 438, and a radially inner side 440. The second end 434 may be disposed opposite the first end 432 in the direction from the first surface 412 toward the second surface 414 (the "−" Z direction). In this manner, the first end 432 may be disposed closer to the first surface 412, and the second end 434 may be disposed closer to the second surface 414. In some embodiments, as shown, each of the barbs 430 may have a height from the first end 432 to the second end 434 (in the Z direction) that is less than each of a first distance from the first end 432 to the first surface 412 (in the Z direction) and a second distance from the second end 434 to the second surface 414 (in the Z direction). Other relative sizes and configurations of the barbs 430, the first planar surface 426, and the second planar surface 428 may be used in other embodiments.

Each of the barbs 430 may include an end surface 444, a first lateral side surface 446, a second lateral side surface 448, and a radially inner surface 450. As shown, the end surface 444 may be disposed at the second end 434 of the barb 430 and may be formed as a planar surface extending perpendicular, or substantially perpendicular, to the central axis $A_C$. Although a perpendicular orientation of the end surface 444 is provided in the illustrated embodiment, other orientations transverse to the central axis $A_C$ may be used in other embodiments. As shown, the first lateral side surface 446 may extend along the first lateral side 436 of the barb 430 and be disposed between the first end 432 and the second end 434. In some embodiments, as shown, the first lateral side surface 446 may extend from the first end 432 to the second end 434 and may be formed as a planar surface extending parallel, or substantially parallel, to the central axis $A_C$. In a similar manner, the second lateral side surface 448 may extend along the second lateral side 438 of the barb 430 and be disposed between the first end 432 and the second end 434. In some embodiments, as shown, the second lateral side surface 448 may extend from the first end 432 to the second end 434 and may be formed as a planar surface extending parallel, or substantially parallel, to the central axis $A_C$. In some embodiments, as shown, each of the barbs 430 may have a lateral thickness from the first lateral side surface 446 to the second lateral side surface 448 that is less than the height of the barb 430. As shown, the radially inner surface 450 may extend along the radially inner side 440 of the barb 430 and be disposed between the first end 432 and the second end 434. In some embodiments, as shown, the radially inner surface 450 may extend from the first end 432 to the second end 434 and may be formed as a planar surface that is angled relative to the central axis $A_C$. As shown, the radially inner surface 450 and the central axis $A_C$ may define an acute angle α therebetween. In some embodiments, the acute angle α may be within a range of 5 degrees to 30 degrees, although other values of the acute angle α may be used. Various relative dimensions and configurations of the barbs 430 may be used in accordance with different embodiments.

FIGS. 5A-5F depict a portion of another example medical implant 500 (which also may be referred to as a "medical device" or simply an "implant"). Respective X, Y, and Z axes are shown in the figures to facilitate description of certain features of the illustrated embodiment and relationships therebetween. Certain similarities and differences between the implant 500 and the implant 400 described above will be appreciated from the drawings and the following description. Particular differences relate to the orientation of the barbs with respect to the first surface and the second surface of the structural member. Corresponding reference numbers are used for corresponding features, which generally may be configured in a manner similar to the features described above unless indicated otherwise. In some embodiments, the medical implant 500 may be a stent, such as an intravascular stent, although various other configurations of the implant 500 may be used in other embodiments. In some embodiments, the medical implant 500 may be formed as an elongated structure having a longitudinal axis $A_L$ (extending in the Y direction). For example, when the implant 500 is a stent, the longitudinal axis $A_L$ may be the axis with respect to which the stent radially expands. The implant 500 may include a structural member 510 (which also may be referred to as a "base member" or a "base") and a radiopaque marker 560 (which also may be referred to as a "radiopaque element," a "radiopaque member," a "radiopaque marker insert," a "radiopaque insert," or a "marker insert") that is fixedly connected to the structural member 510. In other words, the radiopaque marker 560 is not intended to be removed from the structural member 510. In some embodiments, the structural member 510 may be a beam of the medical implant 500. For example, when the implant 500 is a stent, the structural member 510 may be a beam of the stent, such as a strut of the stent.

As shown, the structural member 510 may have a first surface 512, a second surface 514 disposed opposite the first surface 512 (in the Z direction), and an opening 520 (which also may be referred to as a "hole," a "through-hole," or an "aperture") that extends from the first surface 512 to the second surface 514 (in the Z direction). The structural member 510 may have a wall thickness between the first surface 512 and the second surface 514 (in the Z direction). In some embodiments, as shown, the structural member 510 may have a constant wall thickness between the first surface 512 and the second surface 514. In some embodiments, as shown in FIG. 5C, the first surface 512 and the second surface 514 may be planar surfaces, and the second surface 514 may extend parallel, or substantially parallel, to the first surface 512. In some embodiments, as shown in FIG. 5D, the first surface 512 and the second surface 514 may be curved surfaces. For such embodiments, references herein to a feature (e.g., an axis, a surface, etc.) extending "perpendicular" to the first surface 512 and/or the second surface 514 mean that the feature extends perpendicular to a tangent of the curved surface at a location where the feature intersects the first surface 512 and/or the second surface 514. In some embodiments, the first surface 512 and the second surface 514 may be partial-cylindrical surfaces that define the longitudinal axis $A_L$ of the implant 500. In some embodiments, the first surface 512 may be an external surface of the implant 500, and the second surface 514 may be an internal surface of the implant 500. For example, when the implant 500 is a stent, the first surface 512 may be a radially outer surface of the implant 500, and the second surface 514 may be a radially inner surface of the implant 500. The opening 520 may have a central axis $A_C$ extending (in the Z direction) through a center of the opening 520. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 512 and the second surface 514. In some embodiments, when the implant 500 is a stent, the opening 520 may be an eyelet of the stent. In some embodiments, as shown in FIG. 5F, the radiopaque marker 560 may fill the opening 520. In some embodiments, the radiopaque marker 560 may be flush with each of the first surface 512 and the second surface 514, as shown.

The opening 520 may be defined by a plurality of surfaces and/or edges. For example, the opening 520 may be defined by a plurality of curved surfaces and a plurality of planar surfaces. According to the illustrated embodiment, the opening 520 may be defined by a first curved surface 522 extending from the first surface 512 to the second surface 514, a second curved surface 524 extending from the first surface 512 to the second surface 514, a first planar surface 526 extending from the first surface 512 to the second surface 514, and a second planar surface 528 extending from the first surface 512 to the second surface 514. In some embodiments, as shown in FIG. 5C, the first curved surface 522 and the second curved surface 524 may be partial-cylindrical surfaces. In some embodiments, as shown in FIG. 5D, the first curved surface 522 and the second curved surface 524 may be partial-frustoconical surfaces. In some embodiments, as shown in FIG. 5C, each of the first planar surface 526 and the second planar surface 528 may extend parallel, or substantially parallel, to the central axis $A_C$. In some embodiments, as shown in FIG. 4D, each of the first planar surface 526 and the second planar surface 528 may be angled relative to the central axis $A_C$ such that an acute angle is defined between each of the first planar surface 526 and the second planar surface 528 and the central axis $A_C$. The first planar surface 526 may be disposed between the first curved surface 522 and the second curved surface 524 (in the circumferential direction around the central axis $A_C$), and the second planar surface 528 may be disposed between the first curved surface 522 and the second curved surface 524 (in the circumferential direction around the central axis $A_C$). As shown, the first planar surface 526 may extend from the first curved surface 522 to the second curved surface 524 (in the circumferential direction around the central axis $A_C$), and the second planar surface 528 may extend from the first curved surface 522 to the second curved surface 524 (in the circumferential direction around the central axis $A_C$). In this manner, a first edge may be defined at an intersection between the first planar surface 526 and the first curved surface 522, a second edge may be defined at an intersection between the first planar surface 526 and the second curved surface 524, a third edge may be defined at an intersection between the second planar surface 528 and the first curved surface 522, and a fourth edge may be defined at an intersection between the second planar surface 528 and the second curved surface 524, with the edges further defining the opening 520. As shown, the first curved surface 522 and the second curved surface 524 may define respective central axes that are coaxial with the central axis $A_C$ of the opening 520. In other words, the central axis $A_C$ may be defined by the first curved surface 522 and the second curved surface 524. Although two (2) curved surfaces and two (2) planar surfaces are shown in the illustrated embodiment as defining the opening 520, three (3), four (4), five (5), six (6), or more curved surfaces and planar surfaces may be used in other embodiments, with each planar surface being disposed between an adjacent pair of curved surfaces in the circumferential direction.

As shown in FIGS. 5A-5F, the structural member 510 may include a plurality of barbs 530 extending into the opening 520 toward the central axis $A_C$ (in the radial direction with respect to the central axis $A_C$). The barbs 530 may be disposed on the planar surfaces 526, 528. For example, as shown, one of the barbs 530 may be disposed on the first planar surface 526, and another of the barbs 530 may be disposed on the second planar surface 528. Although two (2) barbs 530 are shown in the illustrated embodiment, three (3), four (4), five (5), six (6), or more barbs 530 may be used in other embodiments. In some embodiments, two (2) or more barbs 530 may be disposed on one of the planar surfaces 526, 528. As shown, the pair of barbs 530 may be spaced apart from one another in the circumferential direction and disposed opposite one another with respect to the central axis $A_C$, although other arrangements of the pair of barbs 530 may be used. In embodiments in which three or more barbs 530 are provided, the barbs 530 may be arranged in a circumferential array around the central axis $A_C$. In such embodiments, the barbs 530 may be equally spaced apart from one another or spaced apart from one another at unequal spacings in the circumferential direction around the central axis $A_C$. As shown, the barbs 530 may be spaced apart from each of the first surface 512 and the second surface 514. Specifically, the barbs 530 may be spaced apart from the first surface 512 by a first portion of the respective planar surface 526, 528 and may be spaced apart from the second surface 514 by a second portion of the respective planar surface 526, 528. In some embodiments, as shown, the first curved surface 522 and the second curved surface 524 may be devoid of barbs 430.

Figure 5A:
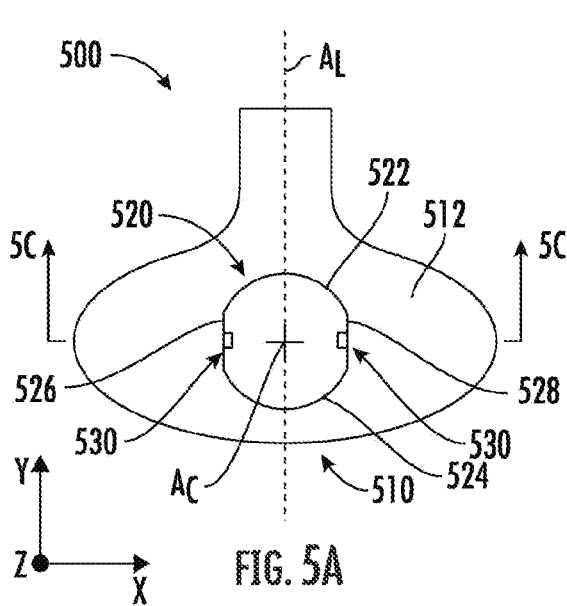
FIG. 5A is a top view of a portion of an example medical implant in accordance with one or more embodiments of the disclosure, the medical implant including a structural member having an opening defined therein and a plurality of barbs.
Figure 5B:
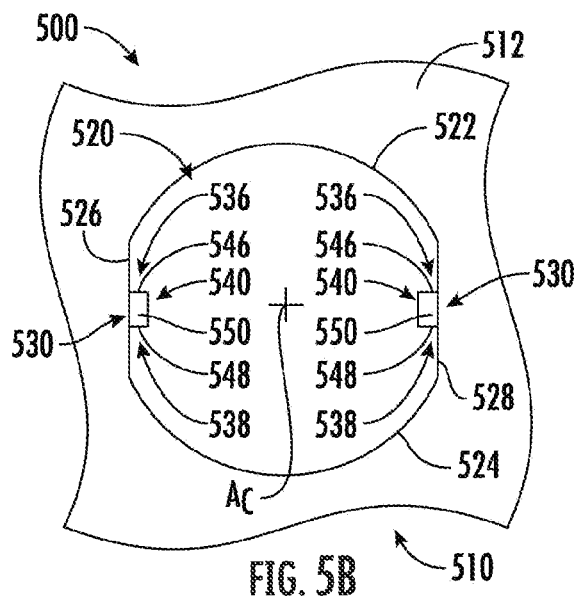
FIG. 5B is a detailed top view of a portion of the medical implant of FIG. 5A, showing the opening and the barbs.
Figure 5C:
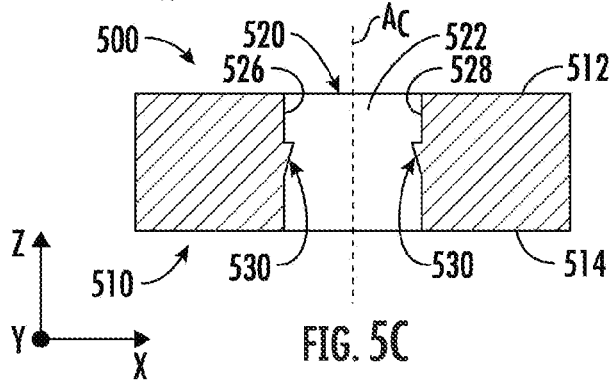
FIG. 5C is a cross-sectional plan view of a portion of the medical implant of FIG. 5A, with the cross-section taken along plane 5C-5C of FIG. 5A.
Figure 5D:
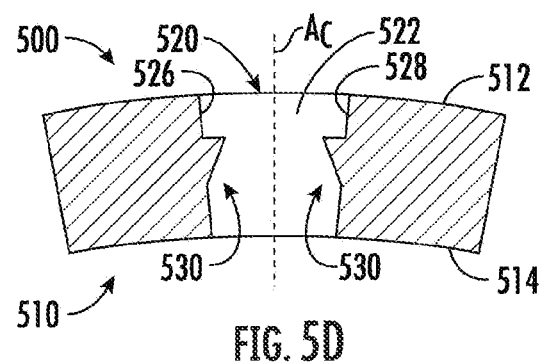
FIG. 5D is a cross-sectional plan view of a portion of the medical implant of FIG. 5A, similar to the cross-section of FIG. 5C.
Figure 5E:
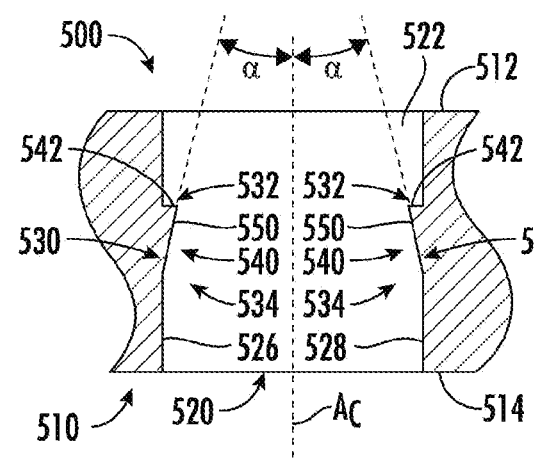
FIG. 5E is a detailed cross-sectional plan view of a portion of the medical implant of FIG. 5A, similar to the cross-section of FIG. 5C, showing the opening and the barbs.
Figure 5F:
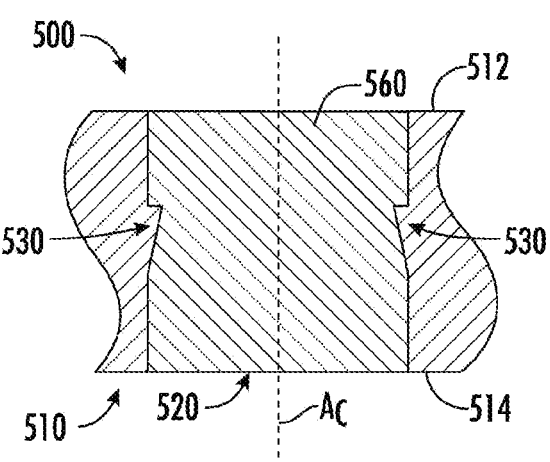
FIG. 5F is a detailed cross-sectional plan view of a portion of the medical implant of FIG. 5A, similar to the cross-section of FIG. 5C, showing the opening, the barbs, and a radiopaque marker disposed within the opening.

As shown in detail in FIGS. 5B and 5E, each of the barbs 530 may have a first end 532, a second end 534, a first lateral side 536, a second lateral side 538, and a radially inner side 540. The second end 534 may be disposed opposite the first end 532 in the direction from the first surface 512 toward the second surface 514 (the "−" Z direction). In this manner, the first end 532 may be disposed closer to the first surface 512, and the second end 534 may be disposed closer to the second surface 514. In some embodiments, as shown, each of the barbs 530 may have a height from the first end 532 to the second end 534 (in the Z direction) that is less than each of a first distance from the first end 532 to the first surface 512 (in the Z direction) and a second distance from the second end 534 to the second surface 514 (in the Z direction). Other relative sizes and configurations of the barbs 530, the first planar surface 526, and the second planar surface 528 may be used in other embodiments.

Each of the barbs 530 may include an end surface 542, a first lateral side surface 546, a second lateral side surface 548, and a radially inner surface 550. As shown, the end surface 542 may be disposed at the first end 532 of the barb 530 and may be formed as a planar surface extending perpendicular, or substantially perpendicular, to the central axis $A_C$. Although a perpendicular orientation of the end surface 542 is provided in the illustrated embodiment, other orientations transverse to the central axis $A_C$ may be used in other embodiments. As shown, the first lateral side surface 546 may extend along the first lateral side 536 of the barb 530 and be disposed between the first end 532 and the second end 534. In some embodiments, as shown, the first lateral side surface 546 may extend from the first end 532 to the second end 534 and may be formed as a planar surface extending parallel, or substantially parallel, to the central axis $A_C$. In a similar manner, the second lateral side surface 548 may extend along the second lateral side 538 of the barb 530 and be disposed between the first end 532 and the second end 534. In some embodiments, as shown, the second lateral side surface 548 may extend from the first end 532 to the second end 534 and may be formed as a planar surface extending parallel, or substantially parallel, to the central axis $A_C$. In some embodiments, as shown, each of the barbs 530 may have a lateral thickness from the first lateral side surface 546 to the second lateral side surface 548 that is less than the height of the barb 530. As shown, the radially inner surface 550 may extend along the radially inner side 540 of the barb 530 and be disposed between the first end 532 and the second end 534. In some embodiments, as shown, the radially inner surface 550 may extend from the first end 532 to the second end 534 and may be formed as a planar surface that is angled relative to the central axis $A_C$. As shown, the radially inner surface 550 and the central axis $A_C$ may define an acute angle α therebetween. In some embodiments, the acute angle α may be within a range of 5 degrees to 30 degrees, although other values of the acute angle α may be used. Various relative dimensions and configurations of the barbs 530 may be used in accordance with different embodiments.

FIGS. 6A-6F depict a portion of another example medical implant 600 (which also may be referred to as a "medical device" or simply an "implant"). Respective X, Y, and Z axes are shown in the figures to facilitate description of certain features of the illustrated embodiment and relationships therebetween. Certain similarities and differences between the implant 600 and the implants 400, 500 described above will be appreciated from the drawings and the following description. Particular differences relate to the shape of the barbs and the presence of multiple end surfaces thereof. Corresponding reference numbers are used for corresponding features, which generally may be configured in a manner similar to the features described above unless indicated otherwise. In some embodiments, the medical implant 600 may be a stent, such as an intravascular stent, although various other configurations of the implant 600 may be used in other embodiments. In some embodiments, the medical implant 600 may be formed as an elongated structure having a longitudinal axis $A_L$ (extending in the Y direction). For example, when the implant 600 is a stent, the longitudinal axis $A_L$ may be the axis with respect to which the stent radially expands. The implant 600 may include a structural member 610 (which also may be referred to as a "base member" or a "base") and a radiopaque marker 660 (which also may be referred to as a "radiopaque element," a "radiopaque member," a "radiopaque marker insert," a "radiopaque insert," or a "marker insert") that is fixedly connected to the structural member 610. In other words, the radiopaque marker 660 is not intended to be removed from the structural member 610. In some embodiments, the structural member 610 may be a beam of the medical implant 600. For example, when the implant 600 is a stent, the structural member 610 may be a beam of the stent, such as a strut of the stent.

As shown, the structural member 610 may have a first surface 612, a second surface 614 disposed opposite the first surface 612 (in the Z direction), and an opening 620 (which also may be referred to as a "hole," a "through-hole," or an "aperture") that extends from the first surface 612 to the second surface 614 (in the Z direction). The structural member 610 may have a wall thickness between the first surface 612 and the second surface 614 (in the Z direction). In some embodiments, as shown, the structural member 610 may have a constant wall thickness between the first surface 612 and the second surface 614. In some embodiments, as shown in FIG. 6C, the first surface 612 and the second surface 614 may be planar surfaces, and the second surface 614 may extend parallel, or substantially parallel, to the first surface 612. In some embodiments, as shown in FIG. 6D, the first surface 612 and the second surface 614 may be curved surfaces. For such embodiments, references herein to a feature (e.g., an axis, a surface, etc.) extending "perpendicular" to the first surface 612 and/or the second surface 614 mean that the feature extends perpendicular to a tangent of the curved surface at a location where the feature intersects the first surface 612 and/or the second surface 614. In some embodiments, the first surface 612 and the second surface 614 may be partial-cylindrical surfaces that define the longitudinal axis $A_L$ of the implant 600. In some embodiments, the first surface 612 may be an external surface of the implant 600, and the second surface 614 may be an internal surface of the implant 600. For example, when the implant 600 is a stent, the first surface 612 may be a radially outer surface of the implant 600, and the second surface 614 may be a radially inner surface of the implant 600. The opening 620 may have a central axis $A_C$ extending (in the Z direction) through a center of the opening 620. In some embodiments, as shown, the central axis $A_C$ may extend perpendicular, or substantially perpendicular, to the longitudinal axis $A_L$. In some embodiments, the central axis $A_C$ may extend perpendicular, or substantially perpendicular, to one or both of the first surface 612 and the second surface 614. In some embodiments, when the implant 600 is a stent, the opening 620 may be an eyelet of the stent. In some embodiments, as shown in FIG. 6F, the radiopaque marker 660 may fill the opening 620. In some embodiments, the radiopaque marker 660 may be flush with each of the first surface 612 and the second surface 614, as shown.

The opening 620 may be defined by a plurality of surfaces and/or edges. For example, the opening 620 may be defined by a plurality of curved surfaces and a plurality of planar surfaces. According to the illustrated embodiment, the opening 620 may be defined by a first curved surface 622 extending from the first surface 612 to the second surface 614, a second curved surface 624 extending from the first surface 612 to the second surface 614, a first planar surface 626 extending from the first surface 612 to the second surface 614, and a second planar surface 628 extending from the first surface 612 to the second surface 614. In some embodiments, as shown in FIG. 6C, the first curved surface 622 and the second curved surface 624 may be partial-cylindrical surfaces. In some embodiments, as shown in FIG. 6D, the first curved surface 622 and the second curved surface 624 may be partial-frustoconical surfaces. In some embodiments, as shown in FIG. 6C, each of the first planar surface 626 and the second planar surface 628 may extend parallel, or substantially parallel, to the central axis $A_C$. In some embodiments, as shown in FIG. 6D, each of the first planar surface 626 and the second planar surface 628 may be angled relative to the central axis $A_C$ such that an acute angle is defined between each of the first planar surface 626 and the second planar surface 628 and the central axis $A_C$. The first planar surface 626 may be disposed between the first curved surface 622 and the second curved surface 624 (in the circumferential direction around the central axis $A_C$), and the second planar surface 628 may be disposed between the first curved surface 622 and the second curved surface 624 (in the circumferential direction around the central axis $A_C$). As shown, the first planar surface 626 may extend from the first curved surface 622 to the second curved surface 624 (in the circumferential direction around the central axis $A_C$), and the second planar surface 628 may extend from the first curved surface 622 to the second curved surface 624 (in the circumferential direction around the central axis $A_C$). In this manner, a first edge may be defined at an intersection between the first planar surface 626 and the first curved surface 622, a second edge may be defined at an intersection between the first planar surface 626 and the second curved surface 624, a third edge may be defined at an intersection between the second planar surface 628 and the first curved surface 622, and a fourth edge may be defined at an intersection between the second planar surface 628 and the second curved surface 624, with the edges further defining the opening 620. As shown, the first curved surface 622 and the second curved surface 624 may define respective central axes that are coaxial with the central axis $A_C$ of the opening 620. In other words, the central axis $A_C$ may be defined by the first curved surface 622 and the second curved surface 624. Although two (2) curved surfaces and two (2) planar surfaces are shown in the illustrated embodiment as defining the opening 620, three (3), four (4), five (5), six (6), or more curved surfaces and planar surfaces may be used in other embodiments, with each planar surface being disposed between an adjacent pair of curved surfaces in the circumferential direction.

As shown in FIGS. 6A-6F, the structural member 610 may include a plurality of barbs 630 extending into the opening 620 toward the central axis $A_C$ (in the radial direction with respect to the central axis $A_C$). The barbs 630 may be disposed on the planar surfaces 626, 628. For example, as shown, one of the barbs 630 may be disposed on the first planar surface 626, and another of the barbs 630 may be disposed on the second planar surface 628. Although two (2) barbs 630 are shown in the illustrated embodiment, three (3), four (4), five (5), six (6), or more barbs 630 may be used in other embodiments. In some embodiments, two (2) or more barbs 630 may be disposed on one of the planar surfaces 626, 628. As shown, the pair of barbs 630 may be spaced apart from one another in the circumferential direction and disposed opposite one another with respect to the central axis $A_C$, although other arrangements of the pair of barbs 630 may be used. In embodiments in which three or more barbs 630 are provided, the barbs 630 may be arranged in a circumferential array around the central axis $A_C$. In such embodiments, the barbs 630 may be equally spaced apart from one another or spaced apart from one another at unequal spacings in the circumferential direction around the central axis $A_C$. As shown, the barbs 630 may be spaced apart from each of the first surface 612 and the second surface 614. Specifically, the barbs 630 may be spaced apart from the first surface 612 by a first portion of the respective planar surface 626, 628 and may be spaced apart from the second surface 614 by a second portion of the respective planar surface 626, 628. In some embodiments, as shown, the first curved surface 622 and the second curved surface 624 may be devoid of barbs 630.

Figure 6A:
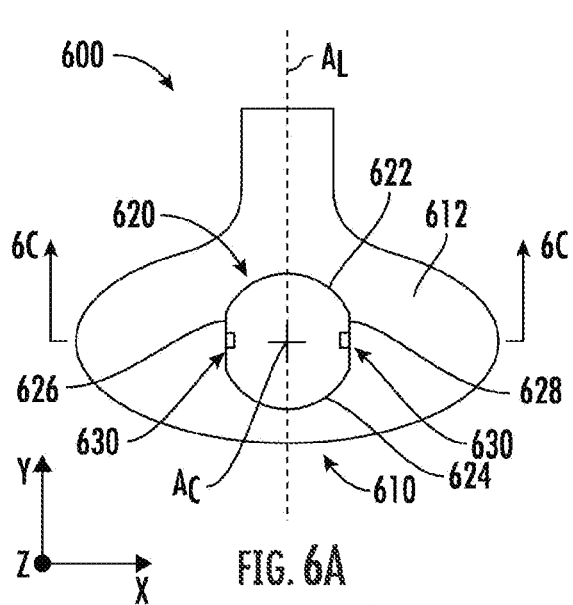
FIG. 6A is a top view of a portion of an example medical implant in accordance with one or more embodiments of the disclosure, the medical implant including a structural member having an opening defined therein and a plurality of barbs.
Figure 6B:
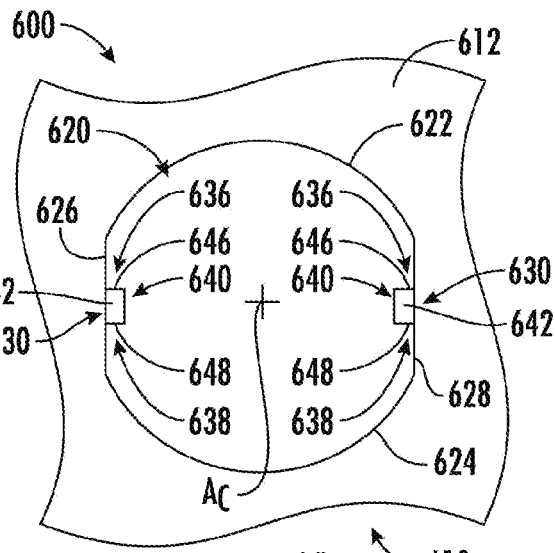
FIG. 6B is a detailed top view of a portion of the medical implant of FIG. 6A, showing the opening and the barbs.
Figure 6C:
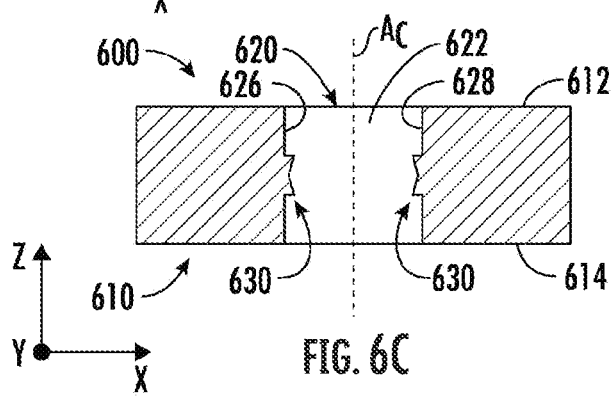
FIG. 6C is a cross-sectional plan view of a portion of the medical implant of FIG. 6A, with the cross-section taken along plane 6C-6C of FIG. 6A.
Figure 6D:
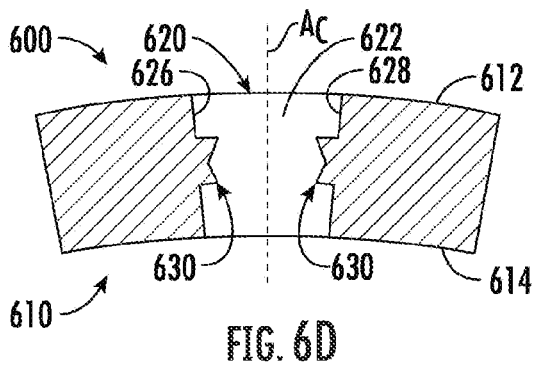
FIG. 6D is a cross-sectional plan view of a portion of the medical implant of FIG. 6A, similar to the cross-section of FIG. 6C.
Figure 6E:
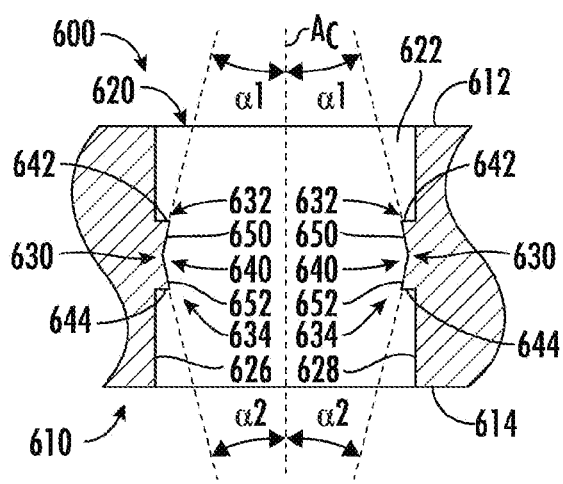
FIG. 6E is a detailed cross-sectional plan view of a portion of the medical implant of FIG. 6A, similar to the cross-section of FIG. 6C, showing the opening and the barbs.
Figure 6F:
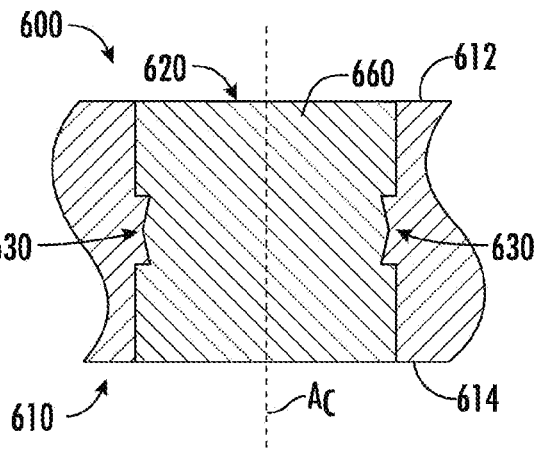
FIG. 6F is a detailed cross-sectional plan view of a portion of the medical implant of FIG. 6A, similar to the cross-section of FIG. 6C, showing the opening, the barbs, and a radiopaque marker disposed within the opening.

As shown in detail in FIGS. 6B and 6E, each of the barbs 630 may have a first end 632, a second end 634, a first lateral side 636, a second lateral side 638, and a radially inner side 640. The second end 634 may be disposed opposite the first end 632 in the direction from the first surface 612 toward the second surface 614 (the "−" Z direction). In this manner, the first end 632 may be disposed closer to the first surface 612, and the second end 634 may be disposed closer to the second surface 614. In some embodiments, as shown, each of the barbs 630 may have a height from the first end 632 to the second end 634 (in the Z direction) that is less than each of a first distance from the first end 632 to the first surface 612 (in the Z direction) and a second distance from the second end 634 to the second surface 614 (in the Z direction). Other relative sizes and configurations of the barbs 630, the first planar surface 626, and the second planar surface 628 may be used in other embodiments.

Each of the barbs 630 may include a first end surface 642, a second end surface 644, a first lateral side surface 646, a second lateral side surface 648, a first radially inner surface 650, and a second radially inner surface 652. As shown, the first end surface 642 may be disposed at the first end 632 of the barb 630 and may be formed as a planar surface extending perpendicular, or substantially perpendicular, to the central axis $A_C$. Although a perpendicular orientation of the first end surface 642 is provided in the illustrated embodiment, other orientations transverse to the central axis $A_C$ may be used in other embodiments. In a similar manner, the second end surface 644 may be disposed at the second end 634 of the barb 630 and may be formed as a planar surface extending perpendicular, or substantially perpendicular, to the central axis $A_C$. Although a perpendicular orientation of the second end surface 644 is provided in the illustrated embodiment, other orientations transverse to the central axis $A_C$ may be used in other embodiments. As shown, the first lateral side surface 646 may extend along the first lateral side 636 of the barb 630 and be disposed between the first end 632 and the second end 634. In some embodiments, as shown, the first lateral side surface 646 may extend from the first end 632 to the second end 634 and may be formed as a planar surface extending parallel, or substantially parallel, to the central axis $A_C$. In a similar manner, the second lateral side surface 648 may extend along the second lateral side 638 of the barb 630 and be disposed between the first end 632 and the second end 634. In some embodiments, as shown, the second lateral side surface 648 may extend from the first end 632 to the second end 634 and may be formed as a planar surface extending parallel, or substantially parallel, to the central axis $A_C$. In some embodiments, as shown, each of the barbs 630 may have a lateral thickness from the first lateral side surface 646 to the second lateral side surface 648 that is less than the height of the barb 630. As shown, the first radially inner surface 650 may extend along the radially inner side 640 of the barb 630 and be disposed between the first end 632 and the second end 634. In some embodiments, as shown, the first radially inner surface 650 may extend from the first end 632 to the second radially inner surface 652 and may be formed as a planar surface that is angled relative to the central axis $A_C$ in a first orientation. As shown, the first radially inner surface 650 and the central axis $A_C$ may define a first acute angle $\alpha 1$ therebetween. In some embodiments, the first acute angle $\alpha 1$ may be within a range of 5 degrees to 30 degrees, although other values of the first acute angle $\alpha 1$ may be used. In a similar manner, the second radially inner surface 652 may extend along the radially inner side 640 of the barb 630 and be disposed between the first end 632 and the second end 634. In some embodiments, as shown, the second radially inner surface 652 may extend from the second end 634 to the first radially inner surface 650 and may be formed as a planar surface that is angled relative to the central axis $A_C$ in a second orientation opposite the first orientation. As shown, the second radially inner surface 352 and the central axis $A_C$ may define a second acute angle α2 therebetween. In some embodiments, the second acute angle α2 may be within a range of 5 degrees to 30 degrees, although other values of the second acute angle α2 may be used. In some embodiments, as shown, the second acute angle α2 may be equal to the first acute angle α1, although different values of the second acute angle α2 and the first acute angle α1 may be used in other embodiments. In some embodiments, each of the barbs 630 may have a symmetrical shape. For example, as shown, the shape of each of the barbs 630 may be symmetrical about the intersection between the first radially inner surface 650 and the second radially inner surface 652. Various relative dimensions and configurations of the barbs 630 may be used in accordance with different embodiments.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A medical implant comprising:
a structural member comprising:
 a first surface;
 a second surface disposed opposite the first surface;
 an opening extending from the first surface to the second surface and defining a central axis of the opening, wherein the opening is defined by a first curved surface and a second curved surface, wherein the first curved surface and the second curved surface are cylindrical surfaces or frustoconical surfaces, and wherein the first curved surface and the second curved surface define respective central axes that are coaxial with the central axis of the opening; and
 a plurality of barbs extending into the opening toward the central axis of the opening; and
a radiopaque marker disposed within the opening.

2. The medical implant of claim 1, wherein the first surface and the second surface are planar surfaces, wherein the second surface extends parallel to the first surface, and wherein the central axis of the opening extends perpendicular to each of the first surface and the second surface.

3. The medical implant of claim 1, wherein the first surface and the second surface are curved surfaces, and wherein the central axis of the opening extends perpendicular to each of the first surface and the second surface.

4. The medical implant of claim 1, wherein the first surface and the second surface are partial-cylindrical surfaces defining a longitudinal axis of the medical implant, and wherein the central axis of the opening extends perpendicular to the longitudinal axis.

5. The medical implant of claim 1, wherein the first surface is an external surface of the medical implant, and wherein the second surface is an internal surface of the medical implant.

6. The medical implant of claim 1, wherein the first curved surface and the second curved surface are cylindrical surfaces.

7. The medical implant of claim 1, wherein the first curved surface and the second curved surface are frustoconical surfaces.

8. The medical implant of claim 1, wherein the first curved surface extends from the first surface to the barbs, and wherein the second curved surface extends from the second surface to the barbs.

9. The medical implant of claim 1, wherein the plurality of barbs comprises a first barb and a second barb spaced apart from one another in a circumferential direction around the central axis of the opening.

10. The medical implant of claim 1, wherein each of the first curved surface and the second curved surface is devoid of barbs.

11. The medical implant of claim 1, wherein the radiopaque marker fills the opening.

12. The medical implant of claim 1, wherein the medical implant is a stent, and wherein the opening is an eyelet of the stent.

13. A medical implant comprising:
a structural member comprising:
 a first surface;
 a second surface disposed opposite the first surface;
 an opening extending from the first surface to the second surface and defining a central axis, wherein the opening is defined by:
  a curved surface extending from the first surface to the second surface; and
  a planar surface extending from the first surface to the second surface; and
 a barb disposed on the planar surface and extending into the opening toward the central axis; and
a radiopaque marker disposed within the opening.

14. The medical implant of claim 13, wherein the curved surface is a partial-cylindrical surface.

15. The medical implant of claim 13, wherein the curved surface is a partial-frustoconical surface.

16. The medical implant of claim 13, wherein the radiopaque marker fills the opening.

17. A medical implant comprising:
a structural member comprising:
 a first surface;
 a second surface disposed opposite the first surface;
 an opening extending from the first surface to the second surface and defining a central axis; and
 a barb extending into the opening toward the central axis, wherein the barb comprises:
  a first end;

a second end disposed opposite the first end in a direction from the first surface toward the second surface;

a first radially inner surface disposed between the first end and the second end and angled relative to the central axis in a first orientation, wherein the first radially inner surface and the central axis define a first acute angle therebetween;

a second radially inner surface disposed between the first end and the second end and angled relative to the central axis in a second orientation opposite the first orientation, wherein the second radially inner surface and the central axis define a second acute angle therebetween;

a first end surface disposed at the first end and extending transverse to the central axis; and a second end surface disposed at the second end and extending transverse to the central axis.

18. The medical implant of claim 17, wherein the opening is defined by a first curved surface and a second curved surface, and wherein the barb is disposed between the first curved surface and the second curved surface.

19. The medical implant of claim 17, wherein the opening is defined by a curved surface and a planar surface, and wherein the barb is disposed on the planar surface.

20. The medical implant of claim 17, wherein a radiopaque marker fills the opening.

* * * * *